US010653883B2

(12) United States Patent
Scott

(10) Patent No.: US 10,653,883 B2
(45) Date of Patent: May 19, 2020

(54) IMPLANTABLE MEDICAL DEVICE FOR PROVIDING CHRONIC CONDITION THERAPY AND ACUTE CONDITION THERAPY USING VAGUS NERVE STIMULATION

(71) Applicant: LivaNova USA, Inc., Houston, TX (US)

(72) Inventor: Timothy L. Scott, Sugar Land, TX (US)

(73) Assignee: LivaNova USA, Inc., Houston, TX (US)

( * ) Notice: Subject to any disclaimer, the term of this patent is extended or adjusted under 35 U.S.C. 154(b) by 0 days.

(21) Appl. No.: 15/721,542

(22) Filed: Sep. 29, 2017

(65) Prior Publication Data

US 2018/0099144 A1 Apr. 12, 2018

Related U.S. Application Data

(63) Continuation of application No. 12/359,104, filed on Jan. 23, 2009, now abandoned.

(51) Int. Cl.
| | | |
|---|---|---|
| *A61N 1/36* | (2006.01) | |
| *A61B 5/0476* | (2006.01) | |
| *A61B 5/00* | (2006.01) | |

(52) U.S. Cl.
CPC .......... *A61N 1/361* (2013.01); *A61B 5/0476* (2013.01); *A61B 5/4094* (2013.01);
(Continued)

(58) Field of Classification Search
CPC .............. A61N 1/3605; A61N 1/36053; A61N 1/36135
See application file for complete search history.

(56) References Cited

U.S. PATENT DOCUMENTS

| | | |
|---|---|---|
| 3,760,812 A | 9/1973 | Timm et al. |
| 3,796,221 A | 3/1974 | Hagfors |

(Continued)

FOREIGN PATENT DOCUMENTS

| | | |
|---|---|---|
| CA | 2339971 | 6/2004 |
| EP | 0 402 683 | 12/1990 |

(Continued)

OTHER PUBLICATIONS

Bachman, D. S. et al, "Effects of Vagal Volleys and Serotonin on Units of Cingulate Cortex in Monkeys", Brain Research, vol. 130. 1977. pp. 253-269.

(Continued)

*Primary Examiner* — Alyssa M Alter
(74) *Attorney, Agent, or Firm* — Foley & Lardner LLP

(57) ABSTRACT

Disclosed herein are methods, systems, and apparatus for treating a medical condition in a patient using an implantable medical device (IMD). The IMD is capable of generating a first electrical signal for treating a medical condition, for example epilepsy. The first electrical signal relates to a long term therapy during a first time period in which there is no indication that the patient's brain is in an stable state, the first electrical signal being a microburst stimulation signal. The implantable device is also capable of generating a second electrical signal for treating the medical condition. The second electrical signal relates to a short term therapy during a second time period, in response to an indication that the patient's brain is in an unstable state. The second electrical signal in one example, may be a conventional stimulation signal.

19 Claims, 11 Drawing Sheets

(52) U.S. Cl.
CPC ...... *A61N 1/36082* (2013.01); *A61N 1/36114* (2013.01); *A61B 5/4047* (2013.01)

(56) References Cited

U.S. PATENT DOCUMENTS

| | | | |
|---|---|---|---|
| 4,107,469 A | 8/1978 | Jenkins |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,985 A | 12/1990 | Wells et al. |
| 5,025,807 A | 6/1991 | Zabara |
| 5,081,987 A | 1/1992 | Nigam |
| 5,154,172 A | 10/1992 | Terry et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |
| 5,330,515 A | 7/1994 | Rutecki et al. |
| 5,334,221 A | 8/1994 | Bardy |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras et al. |
| 5,995,868 A | 11/1999 | Dorfmeister et al. |
| 6,002,966 A | 12/1999 | Loeb et al. |
| 6,016,449 A | 1/2000 | Fischell et al. |
| 6,041,258 A | 3/2000 | Cigaina et al. |
| 6,083,249 A | 7/2000 | Familoni |
| 6,101,412 A | 8/2000 | Duhaylongsod |
| 6,104,955 A | 8/2000 | Bourgeois |
| 6,104,956 A | 8/2000 | Naritoku et al. |
| 6,115,628 A | 9/2000 | Stadler et al. |
| 6,132,361 A | 10/2000 | Epstein et al. |
| 6,141,590 A | 10/2000 | Renirie et al. |
| 6,161,044 A | 12/2000 | Silverstone |
| 6,167,311 A | 12/2000 | Rezai |
| 6,175,764 B1 | 1/2001 | Loeb et al. |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,308,102 B1 | 10/2001 | Sieracki et al. |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 | 4/2002 | Dilorenzo |
| 6,366,814 B1 | 4/2002 | Boveja et al. |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,609,025 B2 | 8/2003 | Barrett et al. |
| 6,609,030 B1 | 8/2003 | Rezai |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |

(56) References Cited

U.S. PATENT DOCUMENTS

| | | |
|---|---|---|
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,662,053 B2 | 12/2003 | Borkan |
| 6,668,191 B1 | 12/2003 | Bogeja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,793,670 B2 | 9/2004 | Osorio et al. |
| 6,819,956 B2 | 11/2004 | Dilorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | Dilorenzo |
| 7,231,254 B2 | 6/2007 | Dilorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | Dilorenzo |
| 7,340,302 B1 | 3/2008 | Falkenberg et al. |
| 2003/0181954 A1 | 9/2003 | Rezai |
| 2003/0181958 A1 | 9/2003 | Dobak, III |
| 2003/0181959 A1 | 9/2003 | Dobak, III |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0036377 A1 | 2/2004 | Mezinis |
| 2004/0039424 A1 | 2/2004 | Merritt et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bluger |
| 2005/0113705 A1 | 5/2005 | Fischell et al. |
| 2005/0113744 A1 | 5/2005 | Donoghue et al. |
| 2005/0119703 A1 | 6/2005 | Dilorenzo |
| 2005/0124901 A1 | 6/2005 | Misczynski et al. |
| 2005/0131467 A1 | 6/2005 | Boveja |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |

(56) References Cited

U.S. PATENT DOCUMENTS

| | | |
|---|---|---|
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | Laporte et al. |
| 2005/0187590 A1 | 8/2005 | Boveja et al. |
| 2005/0187593 A1 | 8/2005 | Housworth |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja et al. |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja et al. |
| 2006/0079936 A1 | 4/2006 | Boveja et al. |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | Kenknight et al. |
| 2006/0200206 A1 | 9/2006 | Firlik et al. |
| 2006/0206155 A1 | 9/2006 | Ben-David et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271409 A1 | 11/2006 | Rosenfeld et al. |
| 2006/0293720 A1 | 12/2006 | Dilorenzo |
| 2007/0027486 A1 | 2/2007 | Armstrong |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073346 A1 | 3/2007 | Corbucci |
| 2007/0073355 A1 | 3/2007 | Dilorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson |
| 2007/0100278 A1 | 5/2007 | Frei et al. |
| 2007/0100377 A1 | 5/2007 | Armstrong et al. |
| 2007/0100392 A1 | 5/2007 | Maschino et al. |
| 2007/0100397 A1 | 5/2007 | Seeberger et al. |
| 2007/0100398 A1 | 5/2007 | Sloan |
| 2007/0112393 A1 | 5/2007 | Gliner |
| 2007/0123946 A1 | 5/2007 | Masoud |
| 2007/0135855 A1 | 6/2007 | Foshee et al. |
| 2007/0142862 A1 | 6/2007 | Dilorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | Dilorenzo et al. |
| 2007/0156179 A1 | 7/2007 | S.E. |
| 2007/0156450 A1 | 7/2007 | Roehm et al. |
| 2007/0156626 A1 | 7/2007 | Roehm et al. |
| 2007/0161919 A1 | 7/2007 | Dilorenzo |
| 2007/0162086 A1 | 7/2007 | Dilorenzo |
| 2007/0167991 A1 | 7/2007 | Dilorenzo |
| 2007/0173901 A1 | 7/2007 | Reeve |
| 2007/0179534 A1 | 8/2007 | Firlik et al. |
| 2007/0179584 A1 | 8/2007 | Gliner |
| 2007/0203548 A1 | 8/2007 | Pawelzik et al. |
| 2007/0208212 A1 | 9/2007 | Dilorenzo |
| 2007/0208390 A1 | 9/2007 | Von Arx et al. |
| 2007/0213785 A1 | 9/2007 | Osorio et al. |
| 2007/0233192 A1* | 10/2007 | Craig ............... A61N 1/36082 607/2 |
| 2007/0233193 A1* | 10/2007 | Craig ............... A61N 1/36082 607/2 |
| 2007/0238939 A1 | 10/2007 | Giftakis et al. |
| 2007/0239210 A1 | 10/2007 | Libbus et al. |
| 2007/0239211 A1 | 10/2007 | Lorincz |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |
| 2007/0255330 A1 | 11/2007 | Lee et al. |
| 2007/0255337 A1 | 11/2007 | Lu |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | Dilorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |

(56) References Cited

U.S. PATENT DOCUMENTS

| | | |
|---|---|---|
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | Dilorenzo |
| 2008/0125820 A1 | 5/2008 | Stahmann et al. |
| 2008/0139870 A1 | 6/2008 | Gliner et al. |
| 2008/0146890 A1 | 6/2008 | Leboeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson et al. |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw |
| 2008/0255582 A1 | 10/2008 | Harris |
| 2009/0054795 A1 | 2/2009 | Misczynski et al. |
| 2009/0076567 A1 | 3/2009 | Fowler et al. |
| 2010/0191304 A1* | 7/2010 | Scott .............. A61B 5/0476 607/45 |

FOREIGN PATENT DOCUMENTS

| | | |
|---|---|---|
| EP | 0 713 714 | 5/1996 |
| EP | 1 647 300 | 2/1998 |
| EP | 1 070 518 | 1/2001 |
| EP | 1 120 130 | 1/2001 |
| EP | 1 145 736 A2 | 10/2001 |
| EP | 1 595 497 | 5/2004 |
| EP | 1 486 232 | 12/2004 |
| GB | 2 026 870 | 12/1982 |
| GB | 2 079 610 | 4/1983 |
| WO | WO-93/02744 | 2/1993 |
| WO | WO-94/17771 | 2/1998 |
| WO | WO-98/25688 | 6/1998 |
| WO | WO-00/40143 | 12/1999 |
| WO | WO-01/05467 | 1/2001 |
| WO | WO-01/08749 | 2/2001 |
| WO | WO-00/64336 | 6/2002 |
| WO | WO-03/076010 | 9/2003 |
| WO | WO-03/085546 | 10/2003 |
| WO | WO-2004/036377 A2 | 4/2004 |
| WO | WO-2004/064918 | 8/2004 |
| WO | WO-2004/071575 | 8/2004 |
| WO | WO-2004/075982 | 9/2004 |
| WO | WO-2004/112894 | 12/2004 |
| WO | WO-2005/007120 | 1/2005 |
| WO | WO-2005/007232 | 1/2005 |
| WO | WO-2005/028026 A1 | 3/2005 |
| WO | WO-2005/053788 | 6/2005 |
| WO | WO-2005/067599 | 7/2005 |
| WO | WO-2004/069330 | 8/2005 |
| WO | WO-2005/101282 | 10/2005 |
| WO | WO-2006/014760 | 2/2006 |
| WO | WO-2006/019822 | 2/2006 |
| WO | WO-2006/050144 | 5/2006 |
| WO | WO-2006/055849 | 5/2006 |
| WO | WO-2006/122148 | 11/2006 |
| WO | WO-2007/066343 | 6/2007 |
| WO | WO-2007/115103 | 10/2007 |
| WO | WO-2007/072425 | 11/2007 |
| WO | WO-2007/124126 | 11/2007 |
| WO | WO-2007/124190 | 11/2007 |
| WO | WO-2007/124192 | 11/2007 |
| WO | WO-2007/142523 | 12/2007 |

OTHER PUBLICATIONS

Bohning, D.E. et al, "Feasibility of Vagus Nerve Stimulation-Synchronized Blood Oxygenation Level-Dependent Functional MRI", A journal of Clinical and Laboratory Research: Investigative Radiology; vol. 36, No. 8, Aug. 2001, pp. 470-479.

Boon, Paul et al, "Programmed and Magnet-Induced Vagus Nerve Stimulation for Refractory Epilepsy", Journal of Clinical Neurophysiology vol. 18 No. 5, 2001, pp. 402-407.

Clark, K.B. et al, "Enhanced Recognition Memory Following Vagus Nerve Stimulation in Human Subjects", Nature Neuroscience, vol. 2 No. 1, Jan. 1999, pp. 93-98.

Clark, K.B. et al, "Posttraining Electrical Stimulation of Vagal Afferents with Concomitant Vagal Efferent Inactivation Enhances Memory Storage Processes in the Rat", Neurobiology of Learning and Memory, vol. 70, 364-373, 1998, Art. No. NL983863.

Craig, A.D. (BUD), "Distribution of Trigeminothalamic and Spinothalamic Lamina I Terminations in the Macaque Monkey", The Journal of Comparative Neurology, vol. 477, pp. 119-148, 2004.

DeGiorgo, Christopher M et al, "Vagus Nerve Stimulation: Analysis of Device Parameters in 154 Patients During the Long-Term XE5 Study", Epilepsia, vol. 42 No. 8, 2001, pp. 1017-1020.

Devous, Michael D et al, "Effects of Vagus Nerve Stimulation on Regional Cerebral Blood Flow in Treatment-Resistant Depression", National Institute of Mental Health—42nd Annual NCDEU Meeting: Poster Session II; Poster Abstracts, Jun. 10-13, 2002, 1 page; http://www.numh.nih.gov/ncdeu/abstracts2002/ncdeu2019.cfm.

Dodrill, Ph.D. et al, "Effects of Vagal Nerve Stimulation on Cognition and Quality of Life in Epilepsy", Epilepsy and Behavior, vol. 2, 2001, pp. 46-53.

Fanselow, E.E. et al, "Reduction of Pentylenetetrazole-Induced Seizure Activity in Awake Rats by seizure-Triggered Trigeminal Nerve Stimulation", The journal of Neuroscience, vol. 20 No. 21, Nov. 2000, pp. 8160-8168.

Fromes, G. et al, "Clinical Utility of On-Demand Magnet Use with Vagus Nerve Stimulation", AES Proceedings, date unknown.

George, M.S. et al, "Vagus Nerve Stimulation: A New Tool for Brain Research and Therapy", Society of Biological Psychiatry vol. 47, 2000, pp. 287-295.

George, M.S., et al, "Open Trial of VNS Therapy in Severe Anxiety Disorders", 156th American Psychiatric Association Annual Meeting, May 17-22, 2003.

Hallowitz, R.A. et al, "Effects of Vagal Volleys on Units of Intralaminar and Juxtalaminar Thalaminar Nuclei in Monkeys", Brain Research, vol. 130, 1977, pp. 271-286.

(56) References Cited

OTHER PUBLICATIONS

Harry, J.D. et al, "Balancing Act: Noise is the Key to Restoring the Body's Sense of Equilibrium", IEEE Spectrum, Apr. 2005, pp. 37-41.
Henry, MD, T.E., "Therapeutic Mechanisms of Vagus Nerve Stimulation" Neurology, vol. 59 Suppl. 4, Sep. 2002, pp. S3-S14.
Henry, T.R., et al, "Brain Blood-Flow alterations Induced by Therapeutic Vagus Nerve Stimulation in Partial Epilepsy: I. Acute Effects at High and Low Levels of Stimulation", Epilepsia vol. 39 No. 9, p. 984-990, 1998.
International Search Report and Written Opinion for International Application No. PCT/US2010/021569, dated Apr. 26, 2010, 13 pages.
King, M.D., "Effects of Short-Term Vagus Nerve Stimulation (VNS) on FOS Expression in Rat Brain Nuclei" 58th Annual Scientific Convention of the Society of Biological Psychiatry, May 2003.
Klapper, M.D. et al, "VNS Therapy Shows Potential Benefit in Patients with Migraine and Chronic Daily Headache After 3 to 6 Months of Treatment )Preliminary Results)" 45th Annual Scientific Meeting of the American Headache Society, Jun. 2003.
Koo, B., "EEG Changes with Vagus Nerve Stimulation" Journal of Clinical Neurophysiology, vol. 18 No. 5, Sep. 2001, pp. 434-441.
Labar, D., "Vagus Nerve Stimulation for 1 Year in 269 patients on Unchanged Antiepileptic Drugs" Seizure vol. 13, 2004 pp. 392-398.
Liebman, K.M. et al, "Improvement in Cognitive Function After Vagal Nerve Stimulator Implantation", Epilepsia, vol. 39, Suppl. 6, 1998, 1 page.
Lockard et al., "Feasibility and Safety of Vagal Stimulation in Monkey Model," Epilepsia, vol. 31 (Supp. 2) 1990, pp. S20-S26.
Malow, B.A. et al, "Vagus Nerve Stimulation Reduces Daytime Sleepiness in Epilepsy Patients" Neurology 57, 2001 ages 879-884.
McClintock, P., "Can Noise Actually Boost Brain Power" Physics World Jul. 2002, pp. 20-21.
Mori, T. et al, "Noise-Induced Entrainment and Stochastic Resonance in Human Brain Waves" Physical Review Letters vol. 88, No. 21 (May 2002), pp. 218101-1-218101-4.

Rugg-Gunn, F.J. et al, "Cardiac Arrhythmias in Focal Epilepsy: a Prospective Long-Term Study" www.thelancet.com vol. 364, 2004, pp. 2212-2219.
Rutecki, P. "Anatomical, Physiological, and Theoretical Basis for the Antiepileptic Effect of Vagus Nerve Stimulation" Epilepsia, vol. 31 Suppl. 2, S1-S6, 1990.
Sahin, M et al, "Improved Nerve Cuff Electrode Recordings with Subthreshold Anodic Currents", IEEE Transactions on Biomedical Engineering, vol. 45, No. 8, Aug. 1998, pp. 1044-1050.
Schachter, S.C. et al, "Progress in Epilepsy Research: Vagus Nerve Stimulation", Epilepsia, vol. 39, No. 7, 1998, pp. 677-686.
Tatum, W.O. et al, "Vagus Nerve Stimulation and Drug Reduction" Neurology, vol. 56, No. 4, Feb. 2001, pp. 561-563.
Tatum, W.O. et al, "Ventricular Asystole During Vagus Nerve Stimulation for Epilepsy in Humans" American Academy of Neurology, 1999, p. 1267-1269.
Terry et al, "The Implantable Neurocybernetic Prosthesis System", Pacing and Clinical Electrophysiology, vol. 14, No. 1, Jan. 1991, pp. 86-93.
Tubbs, R.S. et al, "Left-Sided Vagus Nerve Stimulation Decreases Intracranial Pressure Without Resultant Bradycardia in the Pig: A Potential Therapeutic Modality for Humans" Child's nervous System Original Paper, Springer-Verlag 2004.
Valdes-Cruz, A et al, "Chronic Stimulation of the Cat Vagus Nerve Effect on Sleep and Behavior" Progress in Neuro-Psychopharmacology & Biological Psychiatry, vol. 26, 2002, pp. 113-118.
Vonck et al, "The Mechanism of Action of Vagus Nerve Stimulation for Refractory Epilepsy", Journal of Clinical Neurophysiology, vol. 18(5), 2001, pp. 394-401.
Ward, H., M.D. et al, "Treatment-Refractory Obsessive-Compulsive Disorder: Potential Benefit of VNS Therapy", 23rd Annual Conference of the Anxiety Disorders Association of America, 2007.
Woodbury, et al., "Vagal Stimulation Reduces the Severity of Maximal Electroshock Seizures in Intact Rats. Use of a Cuff Electrode for Stimulating and Recording", Pacing and Clinical Electrophysiology, vol. 14, Jan. 1991, pp. 94-107.
Zabara, J. "Inhibition of Experimental Seizures in Canines by Repetitive Vagal Stimulation", Epilepsia vol. 22, No. 6, 1992, pp. 1005-1012.

\* cited by examiner

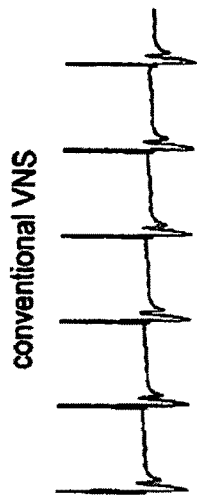
FIGURE 5B
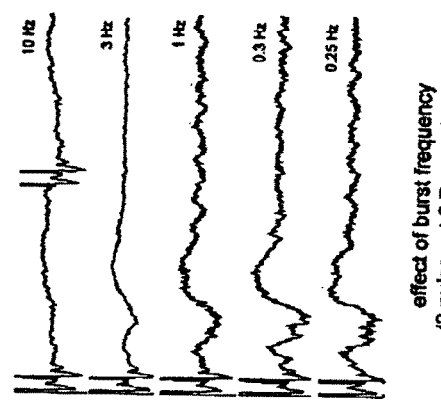
FIGURE 5E
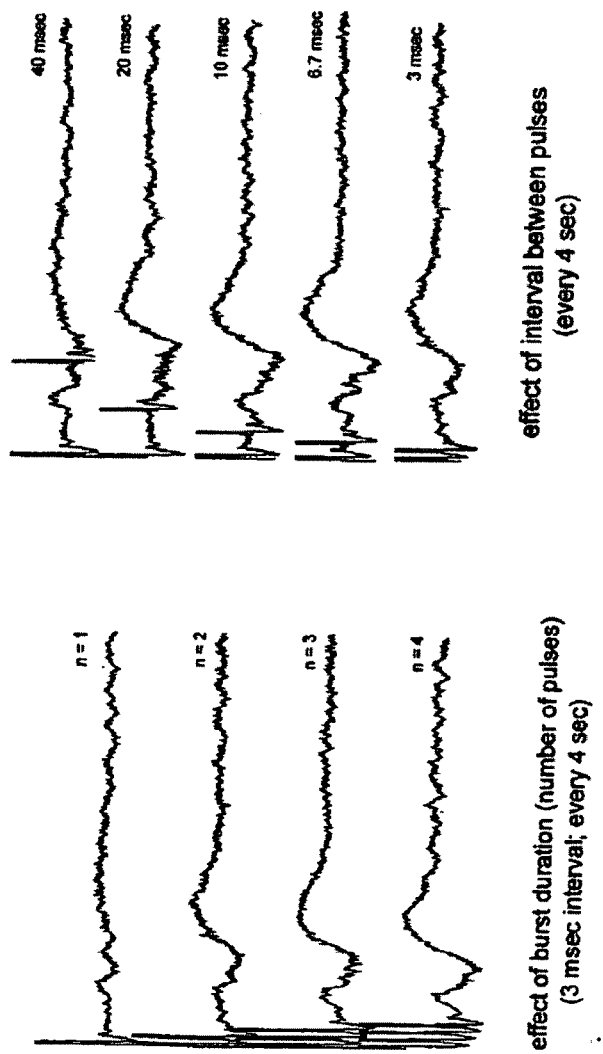
FIGURE 5D
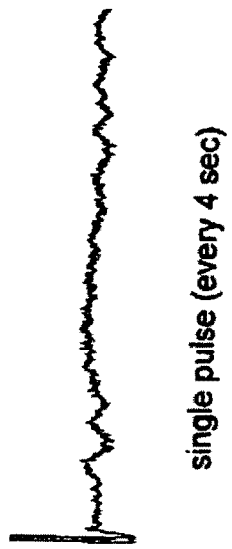
FIGURE 5A
FIGURE 5C

IMPLANTABLE MEDICAL DEVICE FOR PROVIDING CHRONIC CONDITION THERAPY AND ACUTE CONDITION THERAPY USING VAGUS NERVE STIMULATION

CROSS-REFERENCE TO RELATED APPLICATIONS

This application is a continuation of U.S. patent application Ser. No. 12/359,104, filed Jan. 23, 2009, the entire contents of which are incorporated herein by reference.

FIELD OF THE INVENTION

This invention relates generally to medical device systems and, more particularly, to medical device systems for applying electrical signals to a cranial nerve for the treatment of various medical conditions, and for providing a chronic condition therapy and an acute condition therapy using a microburst electrical signal and a non-microburst electrical signal.

DESCRIPTION OF THE RELATED ART

Many advancements have been made in treating diseases such as depression and epilepsy. Therapies using electrical signals for treating these diseases have been found to effective. Implantable medical devices have been effectively used to deliver therapeutic stimulation to various portions of the human body (e.g., the vagus nerve) for treating these diseases. As used herein, "stimulation" or "stimulation signal" refers to the application of an electrical, mechanical, magnetic, electro-magnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuroplasticity or neurogenesis of brain tissue.

In some embodiments, electrical neurostimulation may be provided by implanting an electrical device underneath the skin of a patient and delivering an electrical signal to a nerve such as a cranial nerve. As used in the present application, "open-loop" refers to an electrical signal that is not applied in response to an indication of a need or desire for acute treatment of the patient's medical condition, such as an epileptic seizure detection algorithm based upon one or more sensed body parameters. An open-loop signal is also referred to as a chronic treatment signal. A "closed-loop" signal, on the other hand, refers to an electrical signal that is applied to a target structure in response to an indication of a need or desire for acute treatment of the patient's medical condition. A closed-loop signal is also referred to as an acute treatment signal. The electrical signal may be applied by an IMD that is implanted within the patient's body. In another alternative embodiment, the signal may be generated by an external pulse generator outside the patient's body, coupled by an RF or wireless link to an implanted electrode.

Generally, neurostimulation signals that perform neuromodulation are delivered by the IMD via one or more leads. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal.

While feedback stimulation (i.e., an electrical signal applied in response to a sensed body parameter such as heart rate) schemes have been proposed, conventional vagus nerve stimulation (VNS) usually involves non-feedback stimulation characterized by a number of parameters. Specifically, conventional vagus nerve stimulation usually involves a series of grouped electrical pulses defined by an "on-time" and an "off-time." Each sequence of pulses during an on-time may be referred to as a "pulse burst." The burst is followed by the off-time period in which no signals are applied to the nerve. During the on-time, electrical pulses of a defined electrical current (e.g., 0.5-2.0 milliamps) and pulse width (e.g., 025-1.0 milliseconds) are delivered at a defined frequency (e.g., 20-30 Hz) for the on-time duration, usually a specific number of seconds, e.g., 10-60 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the electrical signal is applied to the nerve.

In conventional VNS, the on-time and off-time may be programmed to define an intermittent pattern in which a repeating series of electrical pulse bursts are generated and applied to a cranial nerve such as the vagus nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation for this purpose. For example, it may be desirable to enhance evoked potentials in the patient's brain to aid in treating a medical condition. Conventional VNS stimulation as described above provides little measurable evoked potentials. It would be desirable to also implement other types of stimulation that significantly increases the evoked potential in the brain as compared to conventional VNS signals.

State of the art IMDs for cranial nerve stimulation generally operate in an open-loop stimulation mode. Generally, IMDs for vagus nerve stimulation (VNS) provide a conventional-type electrical signal, which may include pulse trains that are approximately 30-60 seconds in length at 10-30 Hz, with off-times of from about 7-300 seconds. In this manner, the open-loop VNS modes that provide conventional stimulation may utilize a significant amount of battery life. Further, conventional open-loop VNS consists of a single type of stimulation signal that is provided based upon predetermined parameters. Typically, a physician programs a first type of stimulation signal to be delivered by the IMD for a period of time. After this period of time, further evaluation of the patient's condition may prompt the physician to alter and reprogram the IMD to provide a second stimulation signal different, but largely similar to the first stimulation signal. Regardless of the magnitude of the change, however, the implementation of the second signal is done manually by the physician, and a return to the first signal must likewise be manually implemented by the physician. In this manner, the conventional IMDs for VNS essentially provide just one type of open-loop therapy at a time.

It has been proposed to provide VNS using a combined open-loop and closed-loop stimulation technique with a conventional stimulation signal during an open-loop phase and a slightly altered version of the conventional stimulation signal during a closed-loop stimulation phase. However, such VNS schemes would utilize a greater amount of power than open-loop therapies and thereby affect battery life. The industry generally lacks devices that provide for an efficient stimulation signal during an open-loop cycle and a more robust stimulation signal during a closed-loop cycle, when more robust signals are useful in preventing or attenuating certain epileptic side effects, such as seizures.

SUMMARY OF THE INVENTION

In one aspect of the present invention, a method of treating a medical condition in a patient using an implantable medical device is provided. A first electrical signal characterized by having at least one microburst of a plurality of pulses is applied to a cranial nerve during a first time period to treat the patient's medical condition, which in one embodiment comprises epilepsy. The first time period is a time period during which there is no indication of an acute condition has occurred. In a particular embodiment, the first time period is one in which there is no indication that an epileptic seizure has occurred or is imminent. In another particular embodiment, the first time period is one in which there is no indication that the patient has entered into an unstable brain state. A second electrical signal characterized by at least one burst having a duration and number of pulses greater than a microburst is applied for a second time period in response to an indication of an acute event associated with the medical condition for treating the acute event. In a particular embodiment, the second time period is a treatment period for acute treatment of an epileptic seizure following detection of the actual or imminent occurrence of a seizure. In another particular embodiment, the second time period is a treatment period following detection of the patient experiencing an unstable brain state.

In another aspect of the present invention, a method of treating epilepsy in a patient using an implantable medical device is provided. A programmable electrical signal generator coupled to an electrode is provided. A first electrical signal for providing a chronic stimulation therapy is generated for treating the epilepsy condition. The first elect-Heal signal is a microburst signal and is provided during a first time period in which there is no indication that the patient has entered an unstable brain state. In another embodiment, the first time period is one in which there is no indication of an acute event associated with the medical condition. A second electrical signal for providing an acute stimulation therapy is generated for treating the epilepsy condition. The second electrical signal is a non-microburst signal, and is applied for a second time period in response to an indication that the patient has entered an unstable brain state.

In yet another aspect of the present invention, a system for treating a medical condition in a patient using an implantable medical device is provided. The system includes at least one electrode coupled to at least one cranial nerve of a patient and an implantable medical device operatively coupled to the electrode. The implantable medical device includes a programmable electrical signal generator capable of generating a first electrical signal for providing a chronic stimulation therapy for treating the medical condition. The first electrical signal is a microburst signal and is provided during a first time period in which there is no indication that the patient is experiencing an unstable state. In another embodiment, the first time period is one in which there is no indication of an acute event associated with the medical condition. The implantable device is also capable of generating a second electrical signal for providing an acute stimulation therapy for treating the medical condition. The second electrical signal is a non-microburst signal applied to the at least one cranial nerve for a second time period in response to an indication that the patient has experienced an unstable brain state.

In one embodiment, the present invention provides a computer readable program storage device encoded with instructions that, when executed by a computer, perform a method for treating epilepsy in a patient using an implantable medical device. The method includes applying a first electrical signal to a vagus nerve for a first time period. The first electrical signal is a microburst signal, and the first time period is a time period during which there is no indication that an epileptic seizure has occurred or is imminent. In another embodiment, the first time period is one in which there is no indication of an acute event associated with the medical condition. The method also includes applying to the cranial nerve a second electrical signal for a second time period. The second electrical signal is not a microburst signal, and the second time period is a treatment period for providing an acute treatment of an epileptic seizure following detection of an actual or imminent occurrence of a seizure. In another embodiment, the second time period is a treatment period in response to an indication that the patient has experienced an unstable brain state.

BRIEF DESCRIPTION OF THE DRAWINGS

The invention may be understood by reference to the following description taken in conjunction with the accompanying drawings, in which like reference numerals identify like elements, and in which:

FIGS. 5A-5E show an exemplary comparison of vagal evoked potentials (VEPs) with different stimulus timings;

Figure 1:
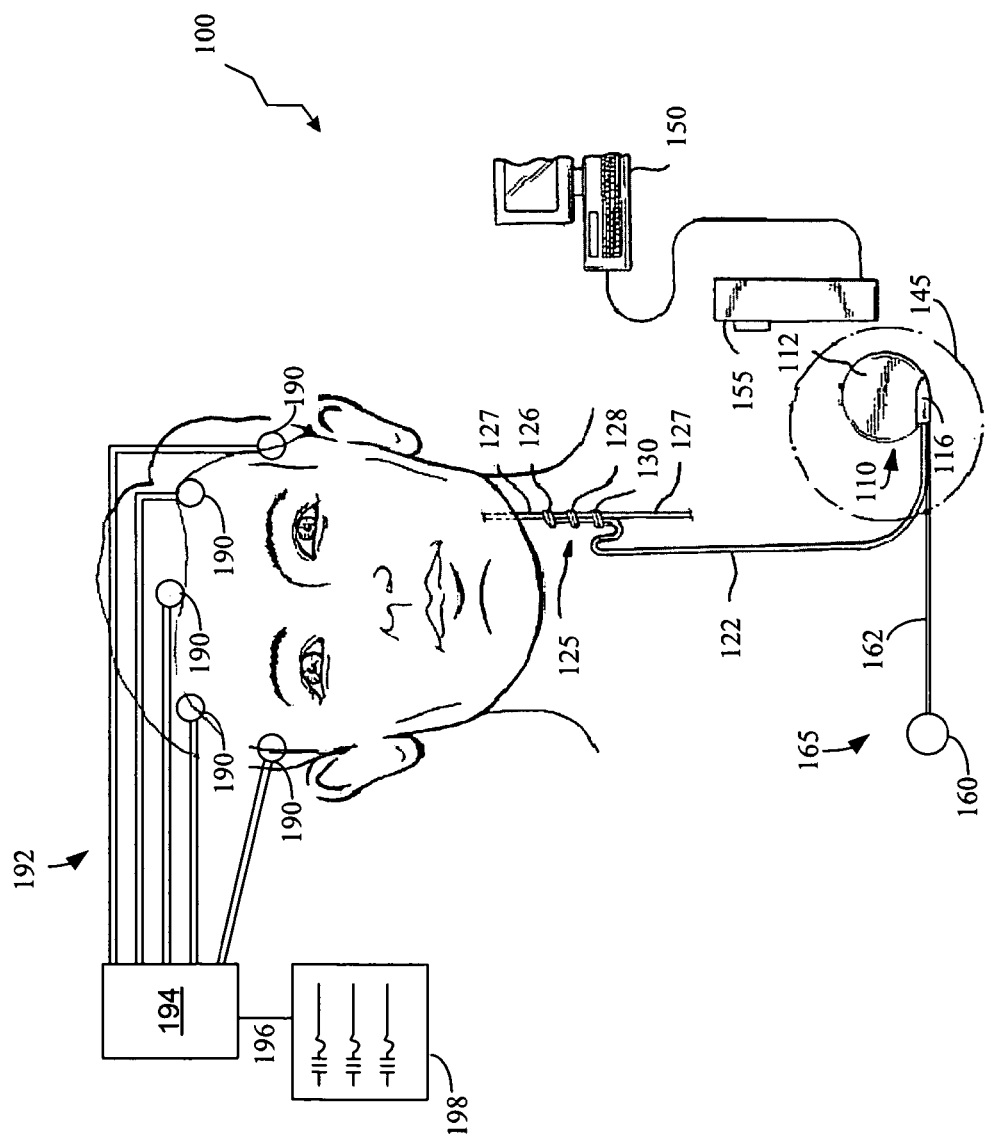
FIG. 1 provides a stylized diagram of an implantable medical device implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain (including neuropathic pain and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which, cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In one embodiment, the present invention provides a method of treating a medical condition. The medical condition can be selected from the group consisting of epilepsy, neuropsychiatric disorders (including but not limited to depression), eating disorders/obesity, traumatic brain injury, coma, addiction disorders, dementia, sleep disorders, pain, migraine, fibromyalgia, endocrine/pancreatic disorders (including but not limited to diabetes), motility disorders, hypertension, congestive heart failure/cardiac capillary growth, hearing disorders (including tinnitus), angina, syncope, vocal cord disorders, thyroid disorders, pulmonary disorders, and reproductive endocrine disorders (including infertility).

Improved therapeutic neurostimulation treatments for a variety of medical conditions have recently been proposed by a new type of electrical stimulation of the cranial nerves capable of providing enhanced evoked potentials in the brain. See, e.g., U.S. Pub. No. 2007/0233193, to Arthur D. Craig ('193 publication). "Enhanced" in the context of the '193 publication refers to electrical potentials evoked in the forebrain by neurostimulation that may be higher than those produced by conventional neurostimulation alone, particularly conventional VNS with an interpulse frequency of 20-30 Hz (resulting in a number of pulses per burst of 140-1800, at a burst duration from 7-60 sec). The electrical signal for the '193 publication is substantially different from the electrical signals in conventional VNS. In particular, the electrical signals in the '193 publication are characterized by very short bursts of a limited number of electrical pulses. These shorts bursts of less than 1 second are referred to hereinafter as "microbursts," and electrical stimulation applying microbursts to a cranial nerve is referred to as "microburst stimulation." By applying an electrical signal comprising a series of microbursts to, for example, a vagus nerve of a patient, enhanced vagal evoked potentials (eVEP) are produced in therapeutically significant areas of the brain.

The present invention involves a combination of microburst and conventional stimulation signals, each of which is used to treat a different aspect of the patient's medical condition. More particularly, in one embodiment, a microburst signal may be used to provide a chronic treatment signal and a conventional stimulation signal may be used to provide an acute treatment signal. In some embodiments, the conventional stimulation signal may be triggered in response to an indication of a need or desire for acute treatment of the patient's medical condition. In other words, in response to an indication that an acute event associated with the medical condition being treated has occurred (e.g., a seizure, an imminent seizure, etc.), a stimulation that is different from the microburst stimulation (e.g., conventional stimulation) may be triggered.

As used herein, the term "microburst" refers to a portion of a therapeutic electrical signal comprising a limited plurality of pulses and a limited duration. More particularly, in one embodiment, a microburst comprises at least two and no more than 25 electrical pulses, preferably at least 2 to and no more than 20 pulses per burst, more preferably at least 2 to and no more than 15 pulses per burst. Microbursts also have a much shorter duration than bursts of a conventional electrical signal. Specifically, in one embodiment, a microburst lasts for no more than 1 second, typically no more than 100 milliseconds, and preferably from about 20 msec to about 80 msec. In one embodiment, a therapeutic microburst electrical signal may comprise a series of microbursts separated from one another by time intervals known as "interburst periods" which allow a refractory interval for the nerve to recover from the microburst and again become receptive to eVEP stimulation by another microburst. In some embodiments, the interburst period may be as long as or longer than the adjacent microbursts separated by the interburst period, but must be at least 100 milliseconds. Adjacent pulses in a microburst are separated by a time interval known as an "interpulse interval." The interpulse interval, together with the number of pulses and the pulse width of each pulse, determines a "microburst duration," which is the length of a microburst from the beginning of the first pulse to the end of the last pulse (and thus the beginning of a new interburst period), and which as noted cannot exceed 1 second.

Microburst electrical signals as used in the new treatment paradigms of the present invention are thus characterized by an interburst period, a microburst duration, a number of pulses per microburst, and an interpulse interval. The pulses in a microburst may be further characterized by a current amplitude and a pulse width. Microburst electrical signals according to the present invention may optionally include an on-time and an off-time in which the microbursts are provided and not provided, respectively, to a cranial nerve. At least one of the interburst period, the burst duration, the number of pulses per microburst, the interpulse interval, the current amplitude, the pulse width, the on-time, or the off-time can be selected to enhance cranial nerve evoked potentials. In addition, as used in the present invention, a microburst electrical signal cannot include any portion of a conventional or non-microburst electrical signal (i.e., pulse bursts having more than 25 pulses, or which exceed 1 second in duration).

In one embodiment, the present invention provides a method of treating a medical condition of a patient using an implantable medical device, comprising applying to a cranial nerve of a patient a pulsed electrical signal comprising delivery of a microburst electrical signal neurostimulation in one time period, as well as conventional neurostimulation in another time period, which are described in more details below. The microburst electrical signal comprises a period of bursts of pulses comprising microbursts as well as interburst periods separating adjacent microbursts. In one embodiment, the interburst periods comprise at least 100 milliseconds each. In another embodiment, the interburst periods comprise at least the length of one of the two microbursts separated by the interburst period. In another embodiment, the interburst period may be determined on a particular patient by providing microbursts separated by increasingly smaller interburst periods. The interburst period may be determined as any time interval greater than that at which the eVEP significantly diminishes or disappears.

It may be convenient to refer to a burst frequency for the microburst electrical signal, defined as 1 divided by the sum of the microburst duration and the interburst period, and it will be recognized by persons of skill in the art that the interburst period may alternatively be described in terms of a frequency of the pulses rather than as an absolute time separating one pulse from another.

Embodiments of the present invention provide for generating a first or primary type of neurostimulation signal during a first time period. The primary type of neurostimulation is an open-loop therapy for applying a chronic therapy signal to a target structure in the patient's body. In one embodiment, the first time period may include a time interval in which a chronic therapy signal is applied in response to a detected cardiac signal, such as heart rate. In another embodiment, the first time period may be a time interval in which a chronic therapy that is a passive electrical signal is applied according to a timed duty cycle, independent of any sensed body parameter. Further, the first or primary type of neurostimulation signal may be a microburst signal, which may be synchronized with the patient's heart rate or may be applied according to a programmed set of parameters such as interburst period, microburst duration, number of pulses per microburst, interpulse interval, current amplitude, and pulse width, independent of any sensed body parameter.

Embodiments of the present invention also include generating a second or secondary type of neurostimulation signal during a second time period. The secondary neurostimulation mode is a closed-loop therapy for applying an acute therapy signal to a target structure in response to an indication of a need or desire for an acute treatment of the patient's medical condition (i.e., acute therapy). The signal indicating a need or desire for acute treatment of the patient's medical condition may include an indication that the patient has experienced an unstable brain state and/or that a seizure has occurred or is imminent. However, in one embodiment, once the secondary stimulation mode is initiated, the termination of this mode may be independent of the continued existence of the signal indicating the need or desire for acute treatment, i.e., the acute treatment may terminate before or after the termination of the signal indicating the need or desire for acute treatment. In other words, in one embodiment, once the secondary neurostimulation mode is initiated, this mode will run a course that is of a pre-determined duration, independent of whether the acute treatment signal that caused the initiation of this mode has changed. That is, the second time period in one embodiment may depend on whether an acute therapy signal is asserted, and in another embodiment, may be independent of the acute therapy signal once it has been asserted and the acute therapy signal initiated. The predetermined duration of the secondary neurostimulation mode may be shorter or longer than the time period when the feedback signal that initiated the secondary neurostimulation mode is asserted.

In another embodiment, after the second time period has elapsed (whether by predetermined time duration or by the discontinuation of a signal indicating need or desire for acute treatment), the patient is again treated by the primary, chronic therapy signal.

In one example, a microburst signal may be provided during a primary, chronic therapy stage having a relatively long duration. A therapy having a longer burst length, such as a conventional-type electrical signal, may be provided during a secondary acute therapy stage having a relatively short duration but corresponding to a need or desire for acute treatment. The primary or chronic therapy may refer to therapy applied during a time period in which no seizure has recently occurred, no seizure is occurring, or no indication of a seizure being imminent is observed. A long-term, primary neurostimulation signal comprising a microburst signal is applied by the IMD during this period.

In one embodiment, a seizure detection algorithm in the IMD may be able to detect whether an epileptic seizure has occurred, is occurring, or is in reasonable probability, imminent. The seizure detection algorithm may involve, e.g., determination of the existence of an unstable brain state associated with an occurring seizure, a seizure that is imminent, or a high probability that a seizure is imminent. Based upon an indication from the seizure detection algorithm of an actual or imminent seizure, or a high probability of an imminent seizure, a closed-loop therapy for treating an acute condition, or an acute therapy signal may be activated by the IMB. In one embodiment, as long at least one parameter indicates that a significant probability exists that a seizure has occurred, is occurring, or is imminent, a second type of neurostimulation, e.g., conventional or more robust stimulation, as opposed to the microburst stimulation, may be provided by the IMB. In another embodiment, the parameter triggers the secondary stimulation mode and the duration of this mode is based upon predetermined parameters and is independent of the duration of the signal indicating the need or desire for acute treatment. The secondary or acute stimulation signal (e.g., conventional vagus nerve stimulation signal) may be defined by a current amplitude, a pulse width, a frequency, an on-time and an off-time to define a non-microburst signal having more than 25 pulses per burst and a burst length exceeding 1 second. In one embodiment, the acute vagus nerve stimulation signal typically has more than 100 pulses per burst and a burst duration of at least about 7 seconds (sec). In another embodiment, the acute vagus nerve stimulation signal has about 100 pulses per burst and a burst duration of at least about 2 sec. During normal operation of the IMD, when there is no indication of a need or desire for acute treatment, a microburst neurostimulation signal is provided by the IMD. Microburst signals may involve lower power consumption than conventional vagus nerve stimulation signals. In one embodiment, the various parameters (e.g., amplitude, frequency, pulse-width, pulse-duration, number of pulses per burst, etc.) of the microburst signal are defined such that treatment of epilepsy is possible.

When the signal indicating a need or desire for acute treatment is asserted, a significant change in the stimulation signal that more resembles conventional stimulation therapy may be triggered to interrupt the seizure, reduce the severity of the seizure, and/or abort the seizure from occurring. Therefore, significant improvement in the patient's quality of life may be realized utilizing the present embodiment. Moreover, embodiments of the present invention may improve therapy by combining microburst stimulation with seizure interruption or prevention capabilities of conventional VNS stimulation. Therefore, improved long-term therapy combined with acute intervention procedures may be provided when the patient is experiencing, or is at immediate threat of a seizure.

The implantable medical device system of one embodiment of the present invention provides for software module(s) that are capable of acquiring, storing, and processing various forms of data, such as patient data/parameters (e.g., physiological data, side-effects data, such as heart rate, breathing rate, brain-activity parameters, disease progression or regression data, quality of life data, etc.) and therapy parameter data. Therapy parameters may include, but are not limited to, electrical signal parameters that define the therapeutic electrical signals delivered by the IMD, medication parameters and/or any other therapeutic treatment parameter. In an alternative embodiment, the term "therapy parameters" may refer to electrical signal parameters defining the therapeutic electrical signals delivered by the IMD. Therapy parameters for a therapeutic electrical signal may also include, but are not limited to, a current amplitude, a pulse width, a frequency, an on-time, an off-time, an interburst period, a number of pulses per burst, an interpulse interval, and a burst duration.

Although not so limited, a system capable of implementing embodiments of the present invention is described below. FIG. 1 depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 may be secured, while retaining the ability to flex with movement of the chest and neck, by a suture connection to nearby tissue (not shown).

In alternative embodiments, the electrode assembly 125 may comprise temperature sensing elements and/or heart rate sensor elements. Other sensors for other body parameters may also be employed to trigger active stimulation. Both passive and active stimulation may be combined or delivered by a single IMD according to the present invention. Either or both modes may be appropriate to treat a specific patient under observation.

In alternative embodiments, a sensor assembly 165, comprising a sensor lead assembly 162 and a sensor 160, may be employed to detect a body parameter of the patient.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

The therapeutic electrical signal described herein may be used to treat a medical condition by enhancing cranial nerve evoked potentials separately, or in combination with another type of treatment. For example, electrical signals according to the present invention may be applied in combination with a chemical agent, such as various drugs, to treat various medical conditions. Further, the electrical stimulation may be performed in combination with treatment(s) relating to a biological or chemical agent. The electrical stimulation treatment may also be performed in combination with other types of treatment, such as magnetic stimulation treatment.

Figure 2:
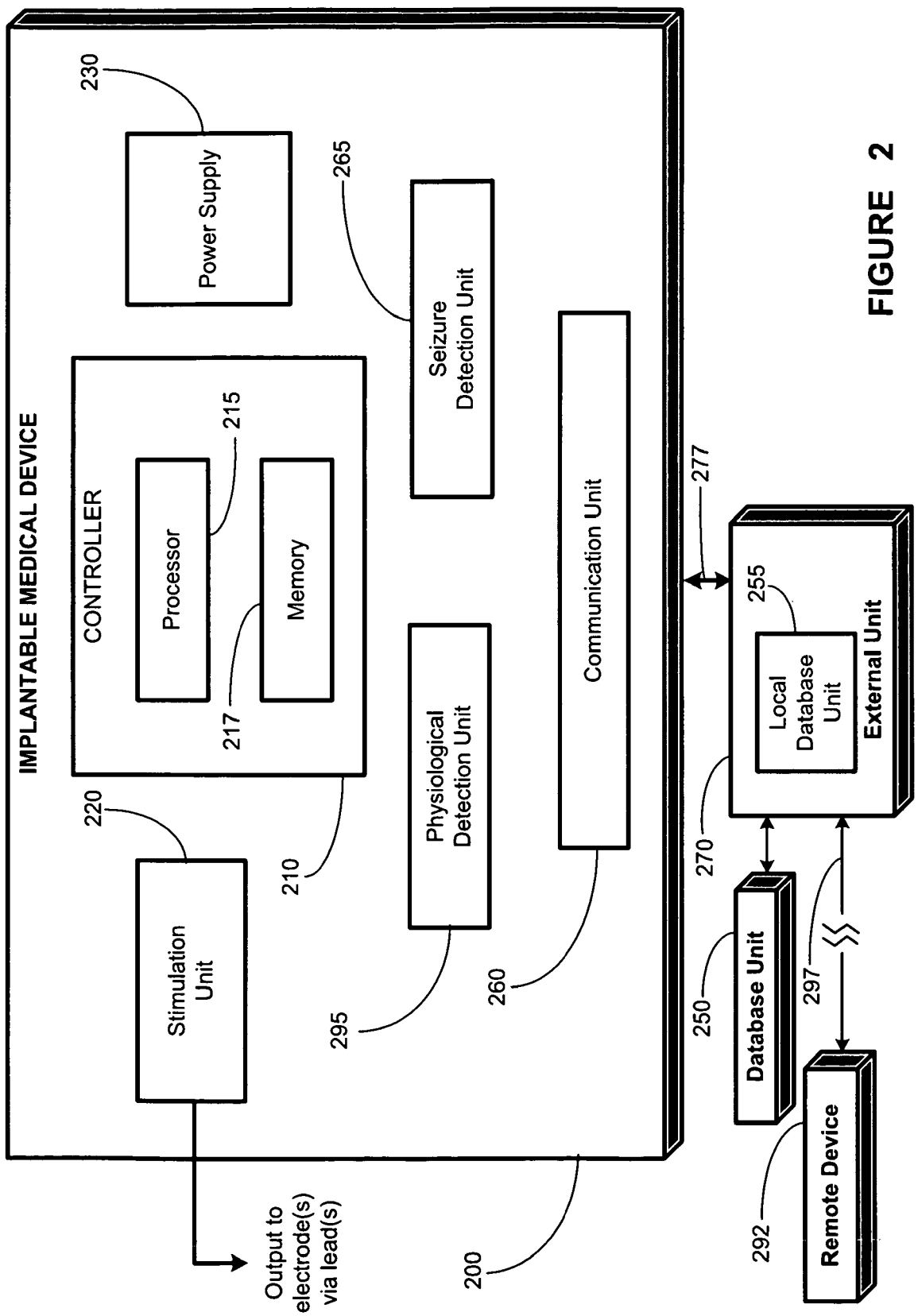
FIG. 2 is a block diagram of a medical device system that includes an implantable medical device and an external device, in accordance with one illustrative embodiment of the present invention.

Turning now to FIG. 2, a block diagram depiction of the IMD 200 is provided, in accordance with one illustrative embodiment of the present invention. The IMD 200 (such as generator 110 from FIG. 1) may comprise a controller 210 capable of controlling various aspects of the operation of the IMD 200. The controller 210 is capable of receiving internal data or external data and causing a stimulation unit 220 to generate and deliver an electrical signal to target tissues of the patient's body for treating a medical condition. For example, the controller 210 may receive manual instructions from an operator externally, or may cause the electrical signal to be generated and delivered based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

The IMD 200 may also comprise a stimulation unit 220 capable of generating and delivering electrical signals to one or more electrodes via leads. A lead assembly such as lead assembly 122 (FIG. 1) may be coupled to the IMD 200. Therapy may be delivered to the leads comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering electrical signals over the leads comprising the lead assembly 122. The stimulation unit 220 is capable of delivering microburst stimulation signals, as well as conventional stimulation signals, and/or variations thereof.

The IMD 200 may also comprise a power supply 230. The power supply 230 may comprise a battery, voltage regulators, capacitors, etc., to provide power for the operation of the IMD 200, including delivering the therapeutic electrical signal. The power supply 230 comprises a power source that in some embodiments may be rechargeable. In other embodiments, a non-rechargeable power source may be used. The power supply 230 provides power for the operation of the IMD 200, including electronic operations and the electrical signal generation and delivery functions. The power supply 230 may comprise a lithium/thionyl chloride cell or a lithium/carbon monofluoride (LiCFx) cell. Other battery types known in the art of implantable medical devices may also be used.

The IMD 200 may also comprise a communication unit 260 capable of facilitating communications between the IMD 200 and various devices. In particular, the communication unit 260 is capable of providing transmission and reception of electronic signals to and from an external unit 270, such as computer 150 and a wand 155 that can communicate with the IMD 200 remotely (FIG. 1). The communication unit 260 may include hardware, software, firmware, or any combination thereof.

In one embodiment, the IMD 200 may also comprise a physiological detection unit 295 that is capable of detecting various patient parameters. For example, the physiological detection unit 295 may comprise hardware, software, or firmware that is capable of obtaining and/or analyzing data relating to one or more body parameters of the patient. This data may include heartbeat data, temperature data, respiratory data, blood pressure data, brain signal data, etc. Based upon the data obtained and/or calculated by the physiological detection unit 295, the IMD 200 may deliver the electrical signal to a portion of the cranial nerve to treat epilepsy, depression or other medical conditions. In one embodiment, the physiological detection unit 295 may also be capable of detecting a manual input from the patient. The manual input may include a magnetic signal input, a tap input, a wireless data input to the IMD 200, etc. The manual input may be indicative of an onset of a seizure.

In one embodiment, the physiological detection unit 295 may comprise hardware, software, or firmware that is capable of obtaining and/or analyzing data relating to one or more body parameters of the patient's cardiac cycle. Based upon the data obtained by the detection unit 295, the IMD 200 may deliver the electrical signal to a portion of the cranial nerve to treat epilepsy, depression or other medical conditions.

The IMD 200 may also comprise a seizure detection unit 265. The seizure detection unit 265 may receive various data from the physiological detection unit 295. As described above, the physiological detection unit may provide various physiological data relating to the patient. Further, physiological detection unit 295 is also capable of detecting input from an external source, such as the patient. Based upon data from the physiological detection unit 295, the seizure detection unit 265 is capable of determining a need or desire for acute treatment of epilepsy, in particular whether a seizure is taking place, whether the seizure has very recently taken place, and/or whether a seizure is imminent. For example, the seizure detection unit 265 may detect a sudden rise in the patient's heart rate, wherein pre-determined/pre-programmed data within the IMD 200 may cause the seizure detection unit 265 to provide an indication that a seizure is impending based upon the received heart rate. In one embodiment, the seizure detection unit 265 is capable of determining that the patient has experienced an unstable brain state associated with the onset, imminent onset, or high probability of the occurrence of a seizure. Based upon this determination, a closed-loop stimulation mode to treat an acute condition or an acute therapy mode may be entered into by the IMD 200. In this closed loop therapy mode or the acute therapy mode, the stimulation unit 220 is capable of delivering a stimulation signal that is a non-microburst stimulation signal, e.g., the conventional style VNS stimulation signals described herein.

When the seizure detection unit 265 provides no indication that there is an impending seizure, actual, or probable seizure, the stimulation unit 220 may then deliver a microburst stimulation signal. In another embodiment, regardless of this indication, once triggered by this indication, the acute therapy mode will run a course that is predetermined, and then revert back to the primary or chronic therapy mode. This process may continue in a primary or chronic therapy mode until the seizure detection unit 265 indicates that a seizure is imminent, actual or highly probable. The seizure detection unit 265 may be preprogrammed using upon various factors, such as physiological characteristics of a particular patient, the anticipated heart-rate deviancy that precedes a seizure, etc. Based upon the indication provided by the seizure detection unit 265, the controller 210 may prompt the stimulation unit 220 to perform an acute therapy stimulation for treating an acute condition utilizing an electrical signal that is not a microburst electrical signal.

The external unit 270 may be a device that is capable of programming electrical signal parameters of the IMD 200. In one embodiment, the external unit 270 is a computer system capable of executing a data-acquisition program. The external unit 270 may be controlled by a healthcare provider, such as a physician, at a base station in, for example, a doctor's office. In alternative embodiments, the external unit 270 may be controlled by a patient in a system providing less control over the operation of the IMD 200 than another external unit 270 controlled by a healthcare provider. Whether controlled by the patient or by a healthcare provider, the external unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, etc. The external unit 270 may download various parameters and program software into the IMD 200 for programming the operation of the IMD, and may also receive and upload various status conditions and other data from the IMD 200. Communications between the external unit 270 and the communication unit 260 in the IMD 200 may occur via a wireless or other type of communication, represented generally by line 277 in FIG. 2. This may occur using, e.g., wand 155 (FIG. 1) to communicate by RF energy with a generator 110. Alternatively, the wand may be omitted in some systems, e.g., systems in which external unit 270 operates in the MICS bandwidths.

In one embodiment, the external unit 270 may comprise a local database unit 255. Optionally or alternatively, the external unit 270 may also be coupled to a database unit 250, which may be separate from external unit 270 (e.g., a centralized database wirelessly linked to a handheld external unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for the primary/chronic therapy and/or secondary/acute therapy modes) using the external unit 270, which may include obtaining and/or analyzing data from the IMD 200 and/or data from the database unit 250 and/or the local database unit 255. The database unit 250 and/or the local database unit 255 may store various patient data.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3:
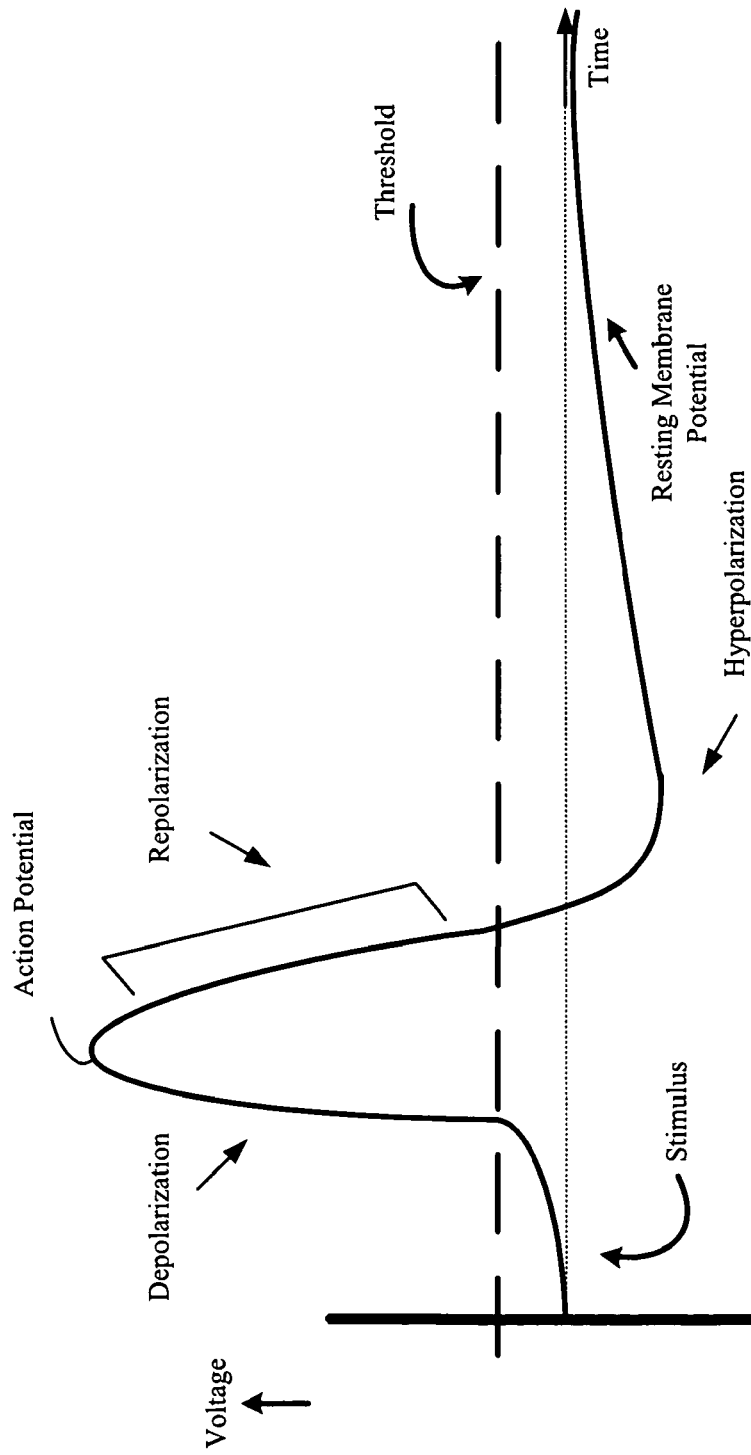
FIG. 3 illustrates an exemplary electrical signal of a firing neuron as a graph of voltage at a given location at particular times in response to application of an electrical signal to the nerve by the neurostimulator of FIG. 2, in accordance with one illustrative embodiment of the present invention.

FIG. 3 provides a stylized depiction of an exemplary electrical signal of a firing neuron as a graph of voltage at a given point on the nerve at particular times during the propagation of an action potential along the nerve, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur.

Referring again to FIG. 1, the IMD 100 may generate a pulsed electrical signal in embodiments of the present invention for application to a cranial nerve such as vagus nerve 127 according to one or more programmed parameters. In one embodiment, the parameters defining the electrical signal may be selected from the group consisting of an interburst period, a number of pulses per burst, an interpulse interval, a burst duration, a current magnitude, a pulse width, an on-time, and an off-time. Suitable ranges for these parameters may comprise a variety of values. In particular, the interburst period in microburst signals according to the present invention is 100 milliseconds or greater, preferably about 1 second to about 5 seconds. In another embodiment, the interburst period may be equal to or greater than the microburst duration of one of the two adjacent microbursts that the interburst period separates. The number of pulses comprising a microburst may range from 2 to 25 pulses, and more specifically from 2 to about 10 pulses. Suitable interpulse intervals in the present invention may range from about 1 millisecond to about 20 milliseconds, more preferably from about 2 milliseconds to about 10 milliseconds. Suitable microburst durations may range from about 2 msec to no more than 1 second, preferably less than about 100 msec, more preferably from about 5 cosec to about 100 msec, and even more preferably from about 20 msec to about 80 msec.

Ranges for current magnitude and pulse width of pulses in a microburst signal may comprise values similar to those for conventional VNS signals, e.g., current magnitudes of 0.10-6.0 milliamps, preferably 0.25-3.0 milliamps, and more preferably 0.5-2.0 milliamps. Pulse widths may range from about 0.05 to about 1.0 milliseconds, preferably 0.25 to about 0.5 milliseconds. In view of the stated values of pulse width and interpulse intervals, a 2-pulse microburst could comprise a microburst duration of as little as 1.1 milliseconds, while a microburst of 25 pulses could last as long as about 500 milliseconds, although microburst durations of 100 milliseconds or less are preferred. In each case, however, the microburst must be less than 1 second in duration.

In one embodiment, microburst signals of the present invention may be applied to the nerve substantially continuously, with microbursts being applied to the nerve separated only by the interburst period (e.g., 1 to 5 seconds in a preferred embodiment) or by second time periods when acute stimulation signals are applied. In an alternative embodiment, the time period in which microburst signals are delivered may at least partially overlap the time period when a secondary (acute therapy), e.g., conventional stimulation signal is applied. In other words, in an alternative embodiment, chronic therapy may overlap at least partially with acute therapy.

Figures 4A, 4B:
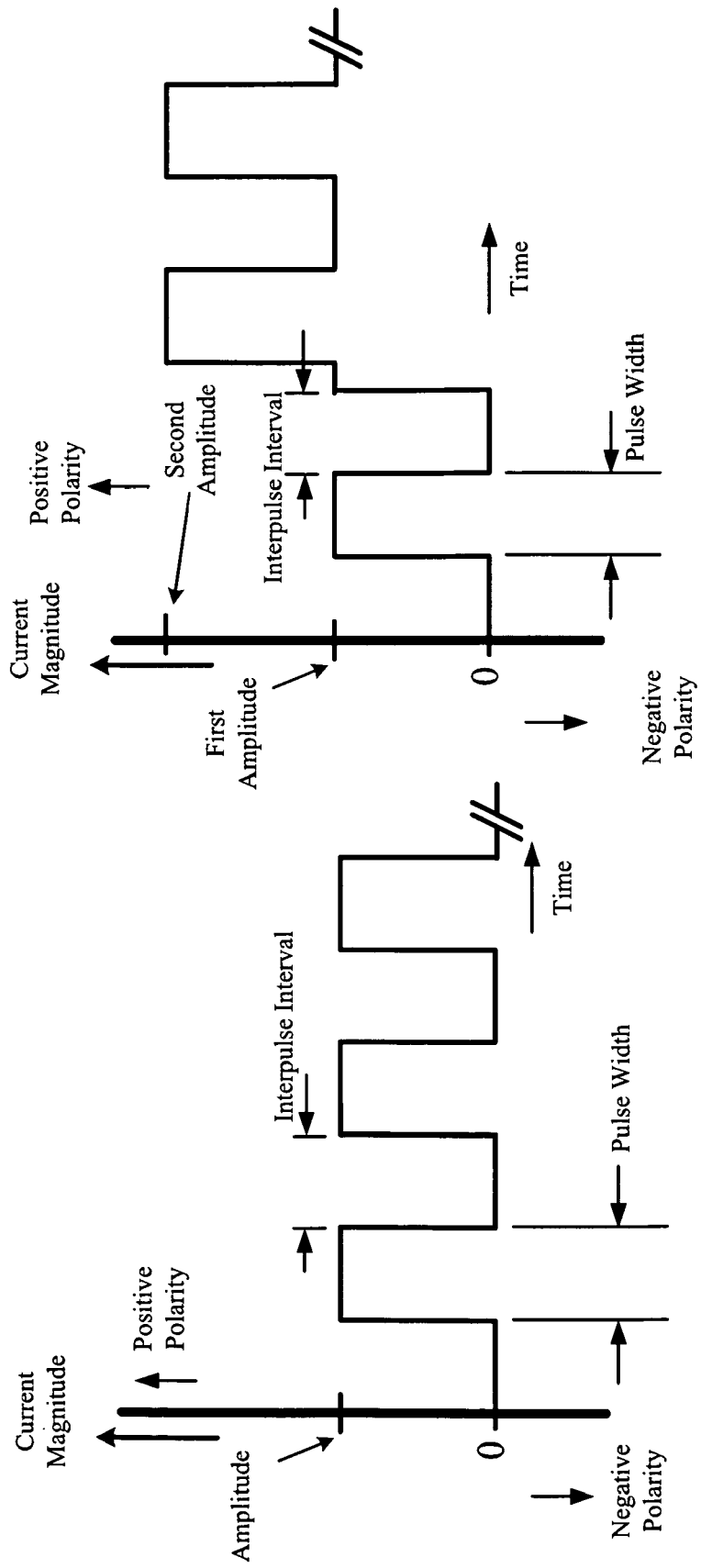
FIGS. 4A, 4B, and 4C illustrate exemplary waveforms for electrical signals for stimulating the cranial nerve for treating a medical condition, according to one illustrative embodiment of the present invention.
Figure 4C:
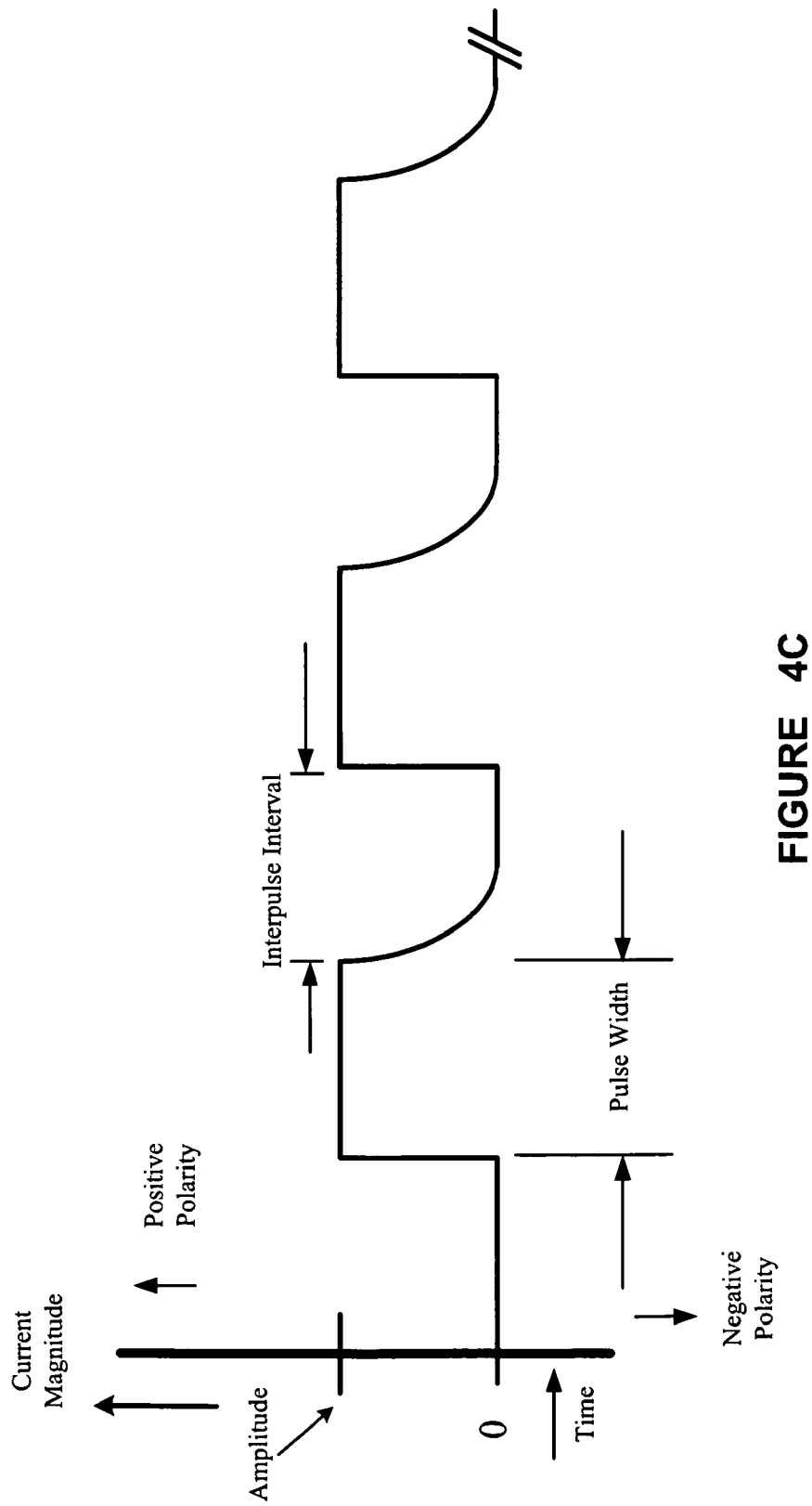

Exemplary pulse waveforms in accordance with one embodiment of the present invention are shown in FIGS. 4A-4C. Pulse shapes in electrical signals according to the present invention may include a variety of shapes known in the art including square waves, biphasic pulses (including active and passive charge-balanced biphasic pulses), triphasic waveforms, etc. In one embodiment, the pulses comprise a square, biphasic waveform in which the second phase is a charge-balancing phase of the opposite polarity to the first phase.

In microburst therapy mode according to the present invention, the microbursts are markedly shorter in both the number of pulses and the microburst duration compared to pulse bursts in conventional neurostimulation signals. While conventional VNS signals typically involve pulse bursts at a frequency of 20-30 Hz for a period of from 7-60 seconds (resulting in a burst having from 140-1800 pulses or more), microbursts according to the present invention, by contrast, can have a microburst duration from about 1 msec to no more than 1 second. Further, each microburst comprises at least 2 and no more than 25 pulses, with each of the pulses separated from an adjacent pulse by an interpulse interval of from about 1 to about 20 milliseconds, more typically from about 2 to about 10 milliseconds. While the individual pulses in a microburst according to this aspect of the invention may resemble conventional VNS signal pulses in pulse width and pulse current, the number of pulses in a microburst is markedly smaller than in a pulse burst in conventional VNS therapy. Consequently, microbursts are also much shorter in duration (less than 1 second and typically less than 100 msec, such as from about 20 msec to about 80 msec) than pulse bursts in conventional neurostimulation therapy (at least 2 seconds and typically 20-60 seconds). More significantly, the physiological effects of the much shorter bursts are very different from conventional bursts in terms of evoked response in the brain. In addition to the much smaller number of pulses and overall duration of microbursts compared to conventional bursts, in most cases, the interpulse interval separating the pulses is shorter than in conventional neurostimulation (typically 2-10 msec for microbursts compared to 30-50 msec for conventional VNS). Pulse bursts of the present invention are termed "microbursts" because they are significantly shorter in both the number of pulses and the total microburst duration than conventional neurostimulation signals.

As noted, it has been discovered that microbursts according to this aspect of the invention are capable of providing an enhanced vagal evoked potential (eVEP) in the patient's brain that is significantly greater than VEPs produced by conventional vagus nerve stimulation signals. This eVEP is attenuated, however, as the number of pulses increases beyond an optimal number of pulses. Thus, for example, in a monkey model discussed below, where a microburst exceeds 2-5 pulses, the eVEP begins to diminish, and eventually disappears. To maintain the eVEP effect, microburst signals require a small number of pulses in a microburst as well as an interburst period separating each microburst from the adjacent microburst in order to allow the nerve a refractory space to recover from the microburst. Providing an appropriate interburst period ensures that the succeeding microburst in the electrical signal is capable of generating an eVEP. In one embodiment the interburst period is as long as or longer than the duration of the adjacent microbursts separated by the interburst period. In another embodiment, the interburst period is at least 100 milliseconds, such as from about 1 sec to about 5 sec. Each microburst comprises a series of pulses that, in some embodiments, are intended to mimic the endogenous afferent activity on the vagus nerve. In one embodiment the microbursts may simulate afferent vagal action potentials associated with each cardiac and respiratory cycle.

Although evoked potentials have been discussed above in the context of the vagus nerve, enhanced evoked potentials can be generated by microburst stimulation of any cranial nerve, e.g. the trigeminal nerve or glossopharyngeal nerve, and remain within the spirit and scope of the present invention. Thus, while the present invention is presented, in certain embodiments, as providing microburst stimulation to a vagus nerve of a patient, microburst stimulation may also be applied to other cranial nerves, particularly the trigeminal nerve and the glossopharyngeal nerve.

The central vagal afferent pathways involve two or more synapses before producing activity in the forebrain. Each synaptic transfer is a potential site of facilitation and a nonlinear temporal filter, for which the sequence of interpulse intervals in a microburst can be optimized. Without being bound by theory, it is believed that the use of microbursts enhances VNS efficacy by augmenting synaptic facilitation and "tuning" the input stimulus train to maximize the forebrain evoked potential.

For example, as shown in FIG. 5, the vagal evoked potential (VEP) measured in the monkey thalamus is scarcely visible if elicited by a single stimulus pulse on the vagus nerve (FIG. 5A), and virtually disappears if the single stimuli are presented in a train at 30 Hz, as in conventional neurostimulation (FIG. 5B). However, as shown in the series of traces in the middle and lower panels of the figure, the VEP is enhanced (resulting in eVEP) by using a microburst of pulses (2-6 pulses per microburst, microburst duration ≤1 second, FIG. 5C) at appropriate interpulse intervals (in this case, 6.7 msec was optimal for the first interpulse interval, shown in FIG. 5D) and at an interburst period (i.e., burst frequency) that approximates the electrocardiogram R-R cycle (the period between R-waves of consecutive heartbeats) in the monkey (in this case 0.3 Hz, shown as FIG. 5E).

The use of pairs of pulses is a physiological tool for producing central responses by stimulation of small-diameter afferent fibers. However, according to one embodiment of the present disclosure, a microburst with an appropriate sequence of interpulse intervals may be used as an effective neurostimulation signal. By selecting an appropriate interburst period, an electrical signal for neurostimulation may comprise a series of microbursts that each provides eVEP. As illustrated in FIG. 5, a microburst of 3-4 pulses produced a maximal VEP in the monkey and a first interpulse interval of ~6-10 msec produced maximal facilitation, and so according to the present disclosure, a microburst of pulses with a total duration of ~10-50 cosec and with an interpulse interval of ~5-10 msec and subsequent microbursts of similar duration with an interburst period of from about 300 cosec to about 3 seconds will produce an optimal VEP in the monkey model. Though not to be bound by theory, the eVEP may result because such a microburst simulates the pattern of action potentials that occur naturally in the small-diameter afferent vagal fibers that elicit the central response that the present enhanced and optimized therapy may evoke (see below). Selection of an appropriate interburst period to separate one microburst from the next may be performed experimentally, although as previously noted, a refractory period of at least 100 msec (such as from 100 msec to 10 min, such as 1 sec to 5 sec) and at least equal to the microburst duration is most desired.

Figure 6:
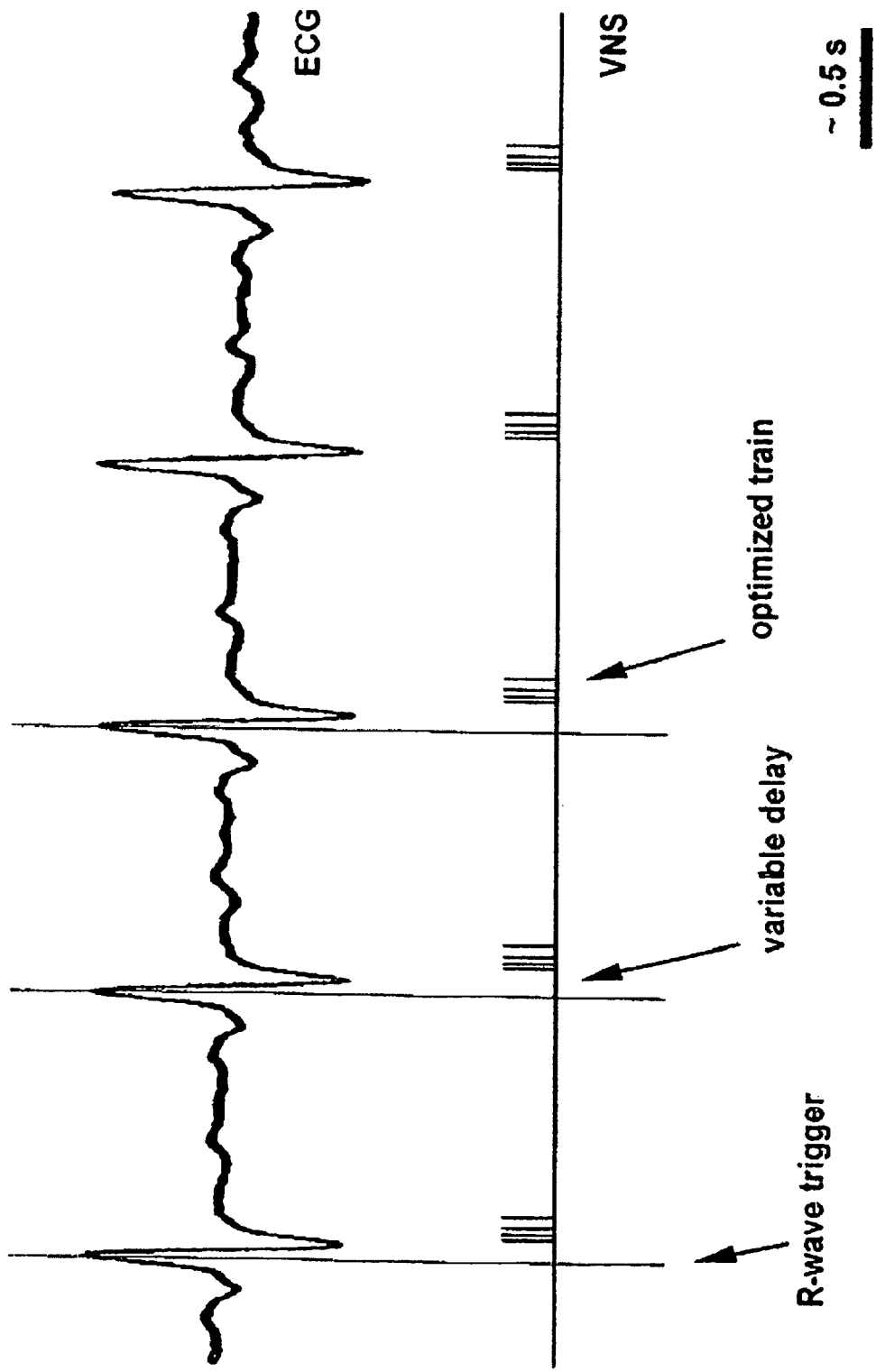
FIG. 6 illustrates a stylized depiction of the synchronization of a vagal stimulus burst to the R-wave of a patient's heartbeat.

The sequence of interpulse intervals may vary with a patient's heart rate variability (HRV) (reflecting cardiac and respiratory timing) and also between individual patients, and thus, in one embodiment, the number of pulses, the interpulse interval, the interburst period, and the microburst duration may be optimized for each patient. As a standard microburst sequence for initial usage, a microburst of 2 or 3 pulses at interpulse intervals of 5-10 msec will approximate the short peak of endogenous post-cardiac activity. The interburst period may also be determined empirically by providing-microbursts with a steadily decreasing interburst period until the eVEP begins to decline, in one embodiment, the interpulse interval between the pulses in an individual microburst is a series of equal intervals (i.e., the simplest train) or increasing intervals, simulating the pattern of a decelerating post-synaptic potential, as illustrated in FIG. 6. In other alternative embodiments, the interpulse intervals may decrease through the microburst, or may be randomly determined within a preselected range, e.g., 5-20 msec. This usage of microburst neurostimulation in combination with conventional neurostimulation during a seizure or an impending seizure, may produce a significant enhancement of neurostimulation efficacy that is applicable to many different medical conditions, such as epilepsy.

In one embodiment, the optimization may be accomplished by recording, using surface electrodes, a far-field VEP, which originates from the thalamus and other regions of the forebrain, and varying the stimulus parameters in order to maximize the recorded potential. As illustrated in FIG. 1, standard EEG recording equipment 194 and 16- or 25-lead electrode placement (of which five electrodes 190 are shown, with leads 192 in electrical communication with the EEG recording equipment 194), such as typically used clinically for recording somatosensory or auditory evoked potentials, will enable the VEP to be recorded and identified as an EEG recording 198. Neurostimulation stimulus burst timing can be used to synchronize averages of 8 to 12 epochs, if desired. By testing the effects of varied numbers of pulses, interpulse intervals, microburst durations, and interburst periods in defining the microbursts, the peak-to-peak amplitude of the eVEP in a microburst can be optimized in each patient.

Neurostimulation can be optimized in individual patients by selected stimulus parameters that produce the greatest effect as measured with EEG surface electrodes. The current amplitude and pulse width is first optimized by measuring the size of the VEP elicited by individual pulses (as opposed to a microburst). The number of pulses, interpulse intervals, microburst durations, and interburst periods for the microbursts are then optimized using the current amplitude and pulse width previously determined, by measuring the size of the eVEP induced by the microbursts. Further measurements using the EEG electrodes may be used to optimize the parameters for the conventional neurostimulation for attenuating a seizure episode and/or reducing the possibility of the onset of a seizure.

Referring again to FIG. 5, the large eVEP recorded in the right thalamus and striatum of the anesthetized monkey using appropriately defined microburst stimulation signals is shown. Without being bound by theory, it is believed that this eVEP is significant for the anti-epileptic effects of neurostimulation, whereas another potential (in the left insular cortex) is most significant for the anti-depression effects of neurostimulation. By using regional EEG localization on the right or left frontal electrodes (FIG. 7), the neurostimulation electrical signal parameters for microbursts, according to this aspect of the invention can be optimized appropriately by measuring the eVEP in these respective regions for individual patients. Regardless of the eVEP provided by microburst signals, conventional type VNS electrical signals may be used during periods when, for example, a seizure detection algorithm employing heart rate parameter (such as a series of R-R intervals), a temperature, an EEG signal, a breathing rate, or an eye parameter, indicates that a seizure has been detected or is imminent. Thus conventional stimulation signals much longer in duration and having a much greater number of pulses per burst than microbursts may be used in response to an indication of a need or desire for acute treatment to interrupt a seizure and/or reduce the severity of an imminent seizure would occur.

The optimal microburst parameters for eliciting eVEPs from these two areas (right thalamus/striatum and left insular cortex, respectively) may differ. Both eVEPs are identifiable with EEG recording methods in awake human patients, so that the appropriate area may easily be used for parametric optimization in an epilepsy or depression patient.

Figure 7:
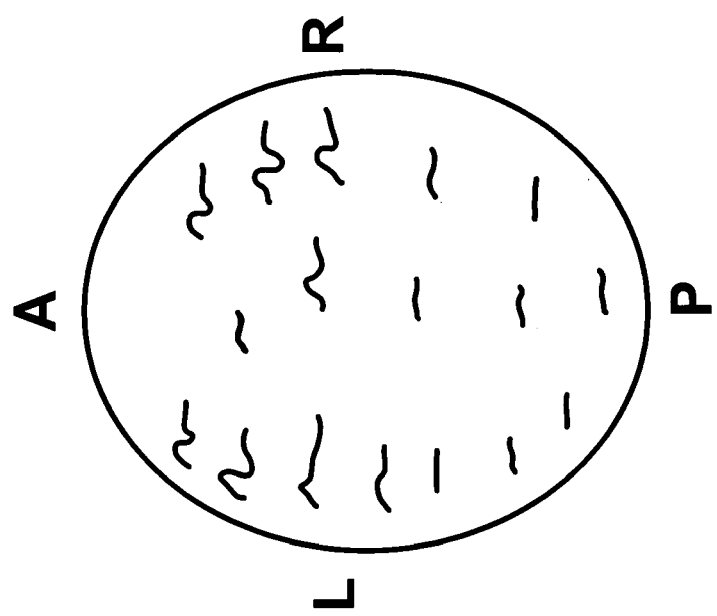
FIG. 7 illustrates the localization of an early VEP in the right thalamus and basal ganglia and a later VEP in the left insular cortex.

The regional EEG localization represented in FIG. 7 allows the early VEP in the right thalamus and basal ganglia associated with the antiepileptic effects of neurostimulation to be distinguished from the later VEP in the left thalamus and insular cortex that may be associated with the treatment of other medical conditions.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to either or both vagus nerves or a branch of either or both vagus nerves. The term "operatively" coupled may include directly or indirectly coupling. Each of the nerves in this embodiment or others involving two or more cranial nerves may be stimulated according to particular activation modalities that may be independent between the two nerves.

Another activation modality for stimulation is to program the output of the IMD 200 to the maximum amplitude which the patient may tolerate. The stimulation may be cycled on and off for a predetermined period of time followed by a relatively long interval without stimulation. Also, the amplitude may vary between microburst and conventional stimulation signals. Where the cranial nerve stimulation system is completely external to the patient's body, higher current amplitudes may be needed to overcome the attenuation resulting from the absence of direct contact with the cranial nerve, such as vagus nerve 127, and the additional impedance of the skin of the patient. Although external systems typically require greater power consumption than implantable ones, they may have an advantage in that their batteries may be replaced without surgery. Moreover, employing microburst signals as the primary, chronic therapy signal and conventional neurostimulation as the secondary, acute therapy may enhance the battery life of the IMD 200.

Returning to systems for providing cranial nerve stimulation, such as that shown in FIGS. 1 and 2, stimulation may be provided in at least two different modalities. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. In this case the IMD 200 may change from microburst neurostimulation to conventional neurostimulation. The patient may manually activate the IMD 200 to stimulate the cranial nerve, such as vagus nerve 127, to treat an acute episode of a medical condition, e.g., a seizure. The patient may also be permitted to alter the intensity of the signals applied to the cranial nerve within limits established by the physician.

Patient activation of an IMD 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for activation of the electrical signal generator 110, e.g., a change from microburst neurostimulation to conventional neurostimulation. Two taps spaced apart by a slightly longer duration of time may be programmed into the IMD 100 to indicate a desire to deactivate the electrical signal generator 110, for example, e.g., change back to microburst neurostimulation from conventional neurostimulation. The patient may be given limited control over operation of the device to an extent which may be determined by the program or entered by the attending physician. The patient may also activate the IMD 100 using other suitable techniques or apparatus.

In some embodiments, feedback stimulation systems other than manually-initiated stimulation may be used in the present invention. A cranial nerve stimulation system may include a sensing lead coupled at its proximal end to a header along with a stimulation lead and electrode assemblies. A sensor may be coupled to the distal end of the sensing lead. The sensor may include a cardiac cycle sensor. The sensor may also include a nerve sensor for sensing activity on a nerve, such as a cranial nerve, such as the vagus nerve 127.

In one embodiment, the sensor may sense a body parameter that may be analyzed to determine a parameter that corresponds to an acute manifestation of the patient's medical condition. If the sensor is to be used to detect a manifestation of the medical condition, a signal analysis circuit may be incorporated into the IMD 200 for processing and analyzing signals from the sensor. Upon detection of the manifestation of the medical condition, the processed digital signal may be supplied to a microprocessor in the IMD 200 to trigger application of an acute electrical signal to the cranial nerve, such as vagus nerve 127. For example, the sensor may sense physiological data (e.g., a sudden change in heart rate) that, after processing by a seizure detection algorithm, may indicate that an epileptic seizure is imminent. In another embodiment, the detection of a manifestation of the medical condition (e.g., a seizure) may trigger an acute electrical signal that is different from a chronic electrical signal. This may entail switching from a microburst to a non-microburst electrical signal.

Figure 8:
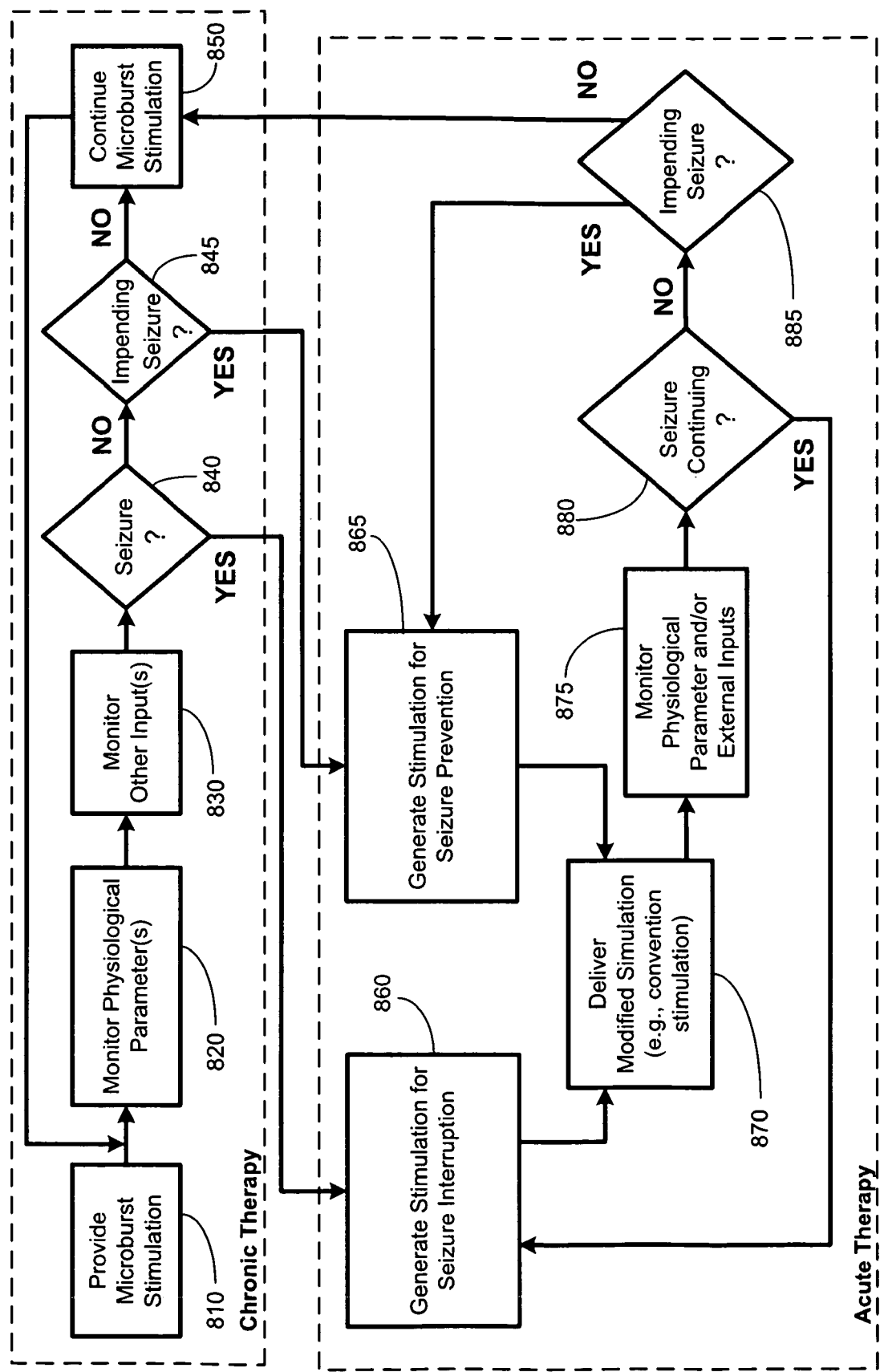
FIG. 8 illustrates a stylized depiction of a chronic stimulation block diagram and an acute stimulation block diagram, according to one illustrative embodiment of the present invention.

Turning now to FIG. 8, a stylized block diagram depiction of the chronic and acute stimulation provided by the IMD 200, in accordance with one illustrative embodiment of the present invention, is provided. FIG. 8 illustrates two separate loops for providing therapy for treating epilepsy using an IMD 200: the chronic therapy, which is an open loop therapy, and the acute therapy, which is a closed loop therapy. In one embodiment, in the chronic therapy mode, the IMD 200 provides a microburst neurostimulation. In one embodiment, the microburst neurostimulation is provided as the primary stimulation for a chronic therapy for treating a medical condition, e.g., epilepsy, depression, eating disorders, etc. Further, the acute therapy is provided to deliver a substantially different stimulation signal as compared to the chronic stimulation as an intervention in response to a determination that an acute manifestation of the medical condition has or will imminently occur. During the acute stimulation mode, a physiological parameter indicative of a seizure, or a possible seizure may be used to control the duration of the acute therapy. In other words, in the embodiment of FIG. 8, as long as the physiological parameter that is indicative of a seizure or a potential seizure is active or asserted, acute stimulation therapy is applied by the IMD 200. In this embodiment, once this parameter is deactivated or de-asserted, the acute therapy mode is terminated and the chronic therapy mode, which provides microburst neurostimulation, is re-activated. The chronic therapy mode is then left active until the acute stimulation signal is once again triggered, i.e., a seizure or imminent seizure is detected.

The IMD 200 provides a microburst neurostimulation signal for treating a chronic condition, e.g., epilepsy, depression, eating disorders, etc (block 810). Microburst neurostimulation relates to the microburst signals described herein. The IMD 200 also performs monitoring of physiological parameters (block 820). In one embodiment, the physiological detection unit 295 is capable of performing analysis and sensing of physiological parameters relating to the patient. Further, the IMD 200 monitors for other inputs, such as external tap inputs, magnet inputs, etc, (block 830). These inputs may also trigger the activation of the acute therapy mode.

Based upon the analysis of the physiological parameters (block 820) and/or external inputs (block 830), the IMD 200 makes a determination whether an acute manifestation of the medical condition, such as a seizure, has occurred (block 840). When the IMD 200 determines that a seizure has not occurred, the IMD 200 also makes a determination whether seizure is imminent (block 845). Together, blocks 840 and 845 determine whether the patient's condition indicates a need or desire for acute treatment. When the IMD 200 determines that an impending seizure is also not present, the IMD 200 continues to maintain a microburst stimulation delivery mode (block 850). In this manner, blocks 810-850 provide a chronic therapy mode, in which microburst signals are delivered for treating a chronic condition, e.g., epilepsy, depression, eating disorders, etc.

Figure 10:
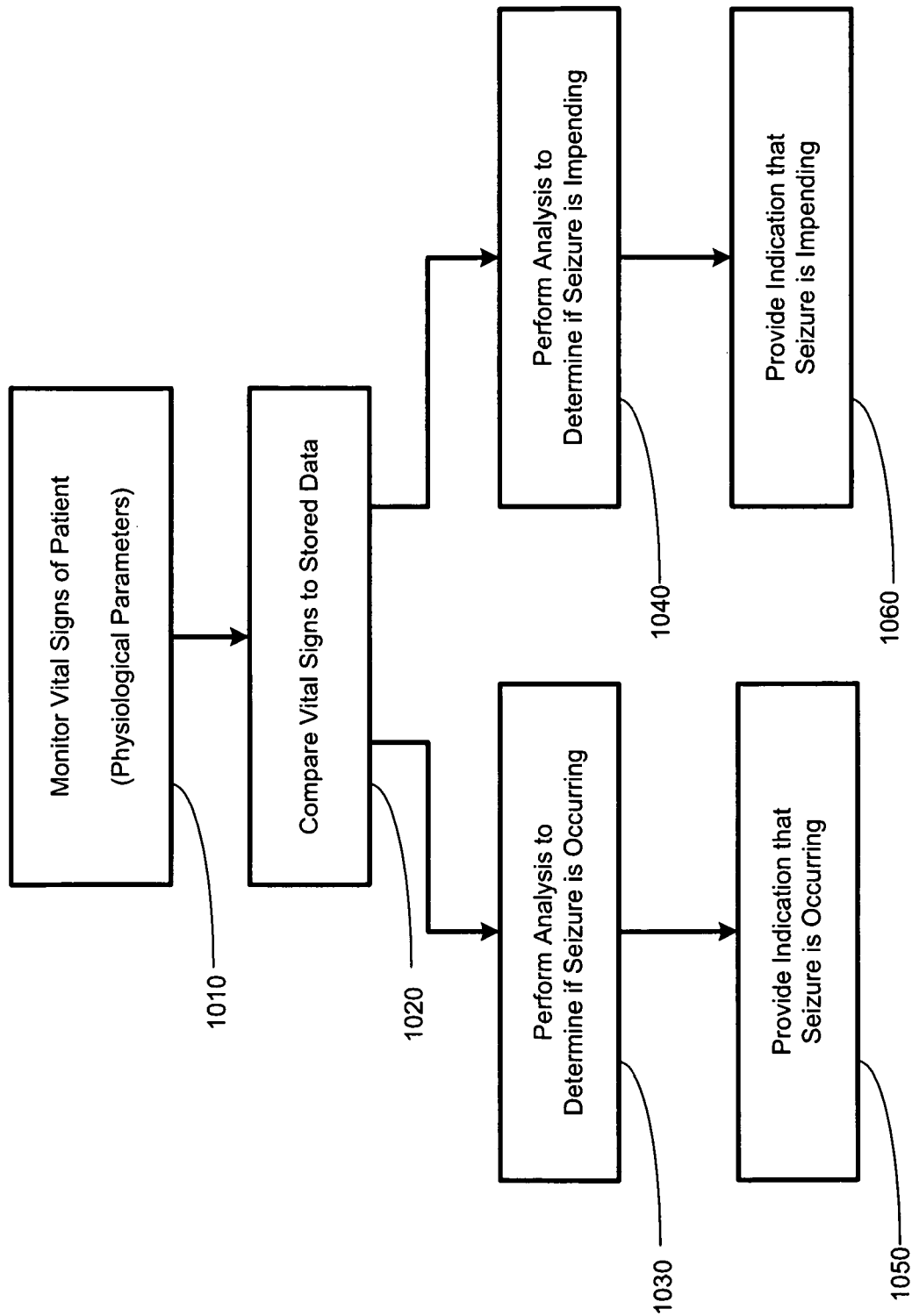
FIG. 10 illustrates a flowchart depiction of a method for monitoring physiological parameters and determining whether an acute manifestation of the medical condition has occurred, in accordance with an illustrative embodiment of the present invention.

FIG. 10 illustrates a stylized block diagram depiction of one embodiment of performing the monitoring of physiological parameters and determining whether an acute manifestation of the medical condition has occurred. The IMD 200 monitors the vital signs of the patient (block 1010). These vital signs may include various physiological parameters, such as heartbeat, respiratory rate, body temperature, blood pressure, etc. The IMD 200 may then compare the detected vital signs/physiological parameters to stored data (block 1020). The stored data may include data for use as thresholds against the detected physiological parameters. Particular thresholds may be preprogrammed into the IMD 200 such that indications of seizures or possible impending seizures may be made based upon comparison of detected physiological data and stored data. In this manner, the IMD 200 performs analysis to determine if a seizure is occurring based upon a comparison of the vital signs/physiological parameters to stored data (block 1030). Further, the IMD 200 may also perform analysis to detect if a seizure is impending based upon the comparison of the vital signs to the stored data (block 1040). For example, a sudden rise in the heart rate may be indicative of a potential impending seizure. Based upon the analysis to determine whether a seizure is occurring, the IMD 200 may provide an indication that a seizure is occurring to the controller 210 (block 1050). Further, based upon the analysis of block 1040, the seizure detection unit 265 may provide an indication that a seizure is impending to the controller 210 (block 1060).

In one embodiment, in the chronic therapy mode, the microburst signal may comprise pulses that are synchronous to the R-wave of the patient's heart beat. For example, a burst of microburst pulses may be delivered to the vagus nerve after a delay period (e.g., about 50 milliseconds) after each R-wave of the patient's heartbeat. However, those skilled in the art, having benefit of the present disclosure would readily appreciate that other delivery of pulses synchronized to the heartbeat may be provided, e.g., synchronizing the bursts to the P-wave, Q-wave, etc. In one embodiment, the bursts may be delivered during varying intervals after the detection of an R-wave, a P-wave, etc. Variations to the delivery of the microburst signals described above may be performed by those skilled in the art having benefit of the present disclosure and still remain within the spirit and scope of the present invention.

FIG. 8 also illustrates an acute stimulation process. Based upon the indication that a seizure is occurring or has occurred (block 840), the IMD 200 may generate a stimulation signal for performing an interruption of the seizure (block 860). In the case where a seizure has recently occurred, a stimulation signal for responding to a previous seizure and/or for preventing a new seizure is provided. This stimulation signal may relate to a more robust signal, as compared to the microburst stimulation. For example, the stimulation of the acute mode may more resemble a conventional, VNS signal and may include a burst with a duration of 5 to 60 seconds at 10-30 Hz. However, various types of signals that are designed to perform an interruption of the seizure of a particular patient, may be pre-programmed into the IMD 200.

Further, in response to a detection that a possible impending seizure may occur (block 845), the IMD 200 may generate a stimulation signal appropriate for preventing or reducing the intensity of an imminent seizure (block 865). In response to a determination that a seizure has occurred or is imminent, the IMD 200 may deliver the modified stimulation, e.g., a conventional stimulation signal, to a portion of the patient's cranial nerve (block 870). While delivering the acute therapy signal, the IMD 200 may continue to monitor physiological parameters and/or inputs from external sources to determine whether to remain within the acute stimulation mode (block 875). Based upon this monitoring, the determination again is made as to whether the seizure is continuing (block 880). Based upon a determination that the seizure is continuing, the IMD 200 continues to generate and apply the acute therapy signal stimulation for interrupting the seizure (See loop from block 880 to block 860).

Further, if the seizure is not found to be continuing or existing, the IMD 200 may further perform a determination whether a seizure is imminent (block 885). If it is determined that a seizure is imminent or highly probable, the IMD 200 may continue to generate and apply the acute therapy signal that is directed to prevent an impending seizure (See loop from block 885 to 865). However, if a seizure is not found to be continuing, and there is no seizure still imminent (block 885), the acute, closed-loop stimulation mode is terminated and the chronic, microburst neurostimulation is re-started (See loop from block 885 to block 850). Blocks 860-885 illustrate an acute therapy mode, wherein further monitoring is performed to determine whether to stay in the acute therapy mode, or whether to exit the acute mode. In this manner, microburst stimulation is provided as a baseline treatment for a chronic condition, e.g., epilepsy; inter-mixed with acute invention using a different stimulation signal (e.g., conventional stimulation) for either preventing an onset of a seizure or treating the seizure. This way, a patient's chronic (e.g., epilepsy) condition is treated using microburst signals, thereby saving power and more significantly, providing a robust stimulation signal when detecting an acute condition, e.g., when a seizure or an impending seizure is detected.

Figure 9:
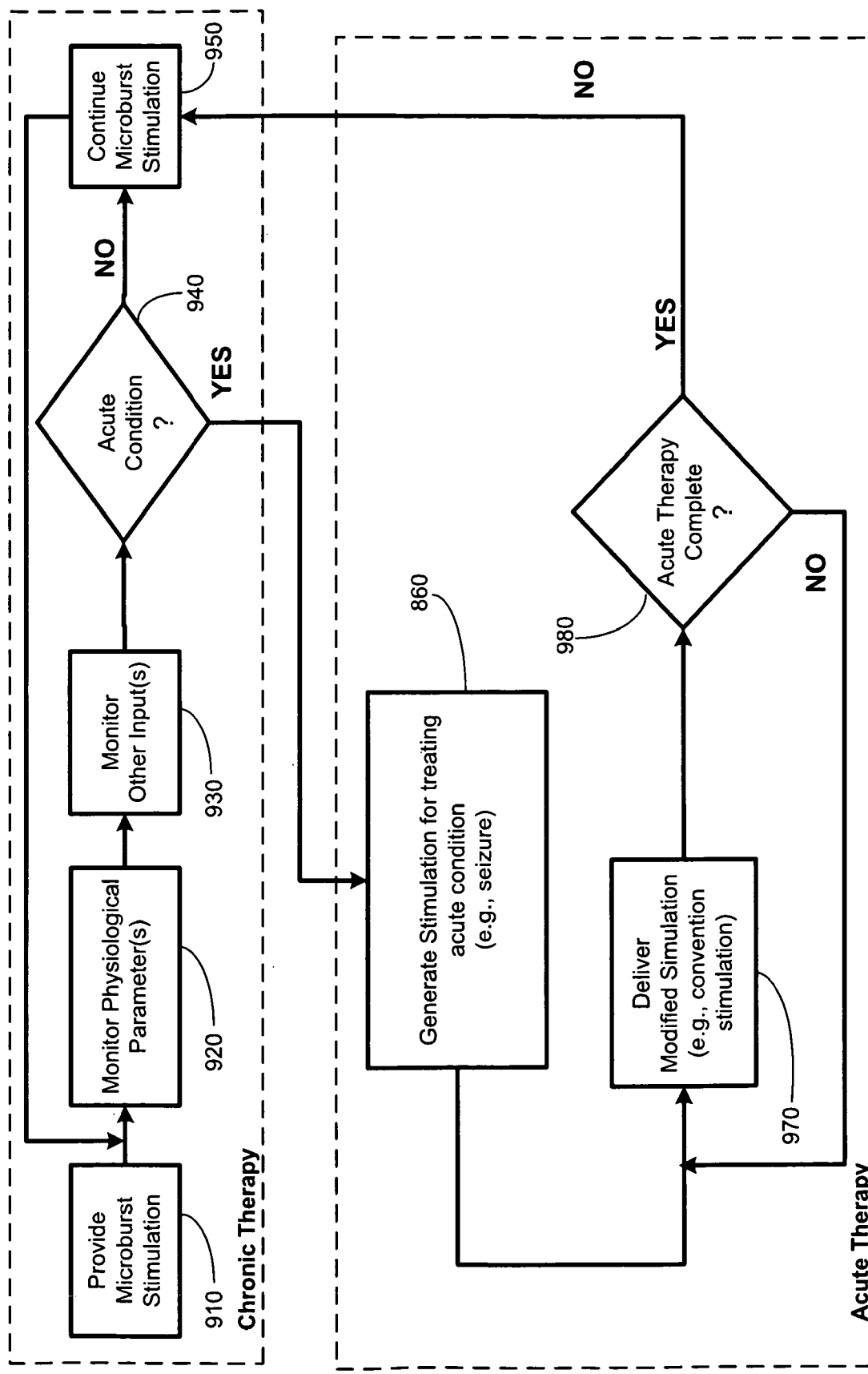
FIG. 9 illustrates a stylized depiction of an chronic stimulation block diagram and an acute stimulation block diagram, according to another illustrative embodiment of the present invention.

Turning now to FIG. 9, a stylized block diagram depiction of the chronic and acute stimulation provided by the IMD 200, in accordance with another illustrative embodiment of the present invention, is provided. FIG. 9 also illustrates two separate loops for providing therapy for treating epilepsy using an IMD 200: the chronic therapy, which is an open loop therapy and the acute therapy, which is a closed loop therapy. In one embodiment, in the chronic therapy mode, the IMD 200 provides a microburst electrical signal. In one embodiment, the microburst neurostimulation is provided as the primary, chronic stimulation for treating a medical condition, e.g., epilepsy, depression, eating disorders, etc. Further, the acute therapy is provided to deliver a substantially different stimulation signal as compared to the chronic therapy signal, as an intervention in response to a determination that an acute manifestation of the medical condition has or will imminently occur. In the embodiment of FIG. 9, the duration of the acute therapy mode is pre-determined and is independent of whether or not an indication of the acute manifestation of the medical condition continues to be asserted. In other words, the detection of the acute condition triggers the acute therapy signal, but does not control the duration of the acute therapy signal.

The IMD 200 provides a microburst neurostimulation signal as a chronic electrical signal for treating a medical condition, e.g., epilepsy, depression, eating disorders, etc (block 910). Microburst neurostimulation relates to the microburst signals described herein. The IMD 200 also performs monitoring of physiological parameters (block 920). In one embodiment, the physiological detection unit 295 is capable of performing analysis and sensing of physiological parameters relating to the patient. Further, the IMD 200 monitors for other inputs, such as external tap inputs, magnet inputs, etc, (block 930). These inputs may also trigger the activation of the acute therapy mode.

Based upon the analysis of the physiological parameters (block 920) and/or external inputs (block 930), the IMD 200 makes a determination whether an acute manifestation of the medical condition has occurred (block 940). In one embodiment, an indication of an acute manifestation of the condition may include an indication that a seizure has occurred or is imminent, or that the patient has entered into an unstable brain state as determined by analysis of EEG, heart rate, temperature, breathing or eye movement/dilation. When the IMD 200 determines that no acute manifestation of the medical condition exists, the IMD 200 continues to maintain a microburst stimulation delivery mode as a chronic therapy (block 950). In this manner, blocks 910-950 provide a chronic therapy mode, in which microburst signals are delivered for treating a medical condition, e.g., epilepsy, depression, eating disorders, etc.

In one embodiment, in the chronic therapy mode, the microburst signal may comprise pulses that are synchronous to the R-wave of the patient's heart beat. For example, a burst of microburst pulses may be delivered to the vagus nerve after a delay period, for example about 50 milliseconds, after each R-wave of the patient's heartbeat. However, those skilled in the art, having benefit of the present disclosure would readily appreciate that other delivery of pulses synchronized to the heartbeat may be provided, e.g., synchronizing the bursts to the P-wave, Q-wave, etc. In one embodiment, the bursts may be delivered during varying intervals after the detection of an R-wave, a P-wave, etc. Variations to the delivery of the microburst signals described above may be performed by those skilled in the art having benefit of the present disclosure and still remain within the spirit and scope of the present invention.

FIG. 9 also illustrates an acute stimulation process. Based upon the indication of an acute condition (block 950), the IMD 200 may generate a stimulation signal that is different from the microburst signal (block 960). For example, the stimulation of the acute mode may more resemble a conventional VNS signal and may include a burst with a duration of 5 to 60 seconds at 10-30 Hz. However, various types of signals that are designed to perform to treat an acute condition may be pre-programmed into the IMD 200. The duration of the acute mode may be also pre-programmed.

The IMD 200 delivers the acute therapy signal to a portion of the patient's cranial nerve (block 970). The IMD 200 then makes a determination whether the time period for completing the acute therapy is finished (block 980). When a determination is made that the acute therapy is not complete, the acute therapy stimulation signal delivery is continued. When a determination is made that the acute therapy is complete, the acute therapy mode is terminated and microburst stimulation signal is delivered (i.e., delivery of chronic therapy neurostimulation is resumed). In this manner, a patient's medical, (e.g., epilepsy) condition is treated using microburst signals as a chronic therapy, thereby saving power providing a first stimulation mode, and more providing a different, non-microburst signal when detecting an acute condition, e.g., when a seizure or an impending seizure is detected. This way, the patient's brain is less likely to adapt to the conventional neurostimulation, since it is only applied in the acute therapy mode, and yet, the patients' medical condition, e.g., epilepsy is treated using microburst neurostimulation. This may preserve the ability of conventional electrical signal to stop an acute condition, such as a seizure, avoiding an adaptation of the brain to an otherwise therapeutically effective signal. Further, in an alternative embodiment, during the off times described above, a small amount of stimulation, i.e., background stimulation that features an electrical signal below the threshold to generate evoked potentials, may be applied.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A method of treating a medical condition in a patient using an implantable medical device, comprising:
    applying, to a cranial nerve, a first electrical signal including at least one microburst of a plurality of pulses during a first time period to treat the medical condition, the first time period being a time period during which there is no indication that an acute condition has occurred;
    detecting an indication of an acute event associated with the medical condition based on at least one factor preprogrammed to the implantable medical device, the at least one preprogrammed factor comprising at least one physiological characteristic particular to the patient; and
    applying, to the cranial nerve, a second electrical signal to treat the medical condition in response to the indication of the acute event and for treating the acute event, the second electrical signal including at least one burst of a second plurality of pulses during a second time period that is a non-microburst, wherein the first time period occurs prior to the second time period.

2. The method of claim 1, further comprising:
    monitoring the at least one physiological characteristic during application of the second electrical signal to determine whether the at least one characteristic is active; and
    in response to determining that the at least one physiological characteristic is not active, reapplying, to the cranial nerve, the first electrical signal.

3. The method of claim 1, wherein the at least one physiological characteristic particular to the patient comprises a heart rate deviancy that precedes a seizure for the patient.

4. The method of claim 1, wherein the indication is an indication that an epileptic seizure has occurred, an indication that the epileptic seizure is substantially imminent, or an indication that an imminent occurrence of the epileptic seizure is highly probable; and
    wherein applying the first electrical signal further comprises applying the first electrical signal to provide a chronic treatment for an epilepsy condition.

5. The method of claim 1, wherein detecting the indication of the acute event comprises:
    sensing at least one body parameter associated with the at least one physiological characteristic; and
    applying a seizure detection algorithm to the at least one sensed body parameter to detect the indication of the acute event;
    wherein the at least one body parameter comprises at least one of a heart rate parameter, a temperature, an EEG signal, a breathing rate, or an eye parameter.

6. The method of claim 1, wherein applying the first electrical signal comprises at least one of applying the microburst pulses in a predetermined pattern or applying the microburst pulses substantially synchronously with a heartbeat of the patient.

7. The method of claim 1, wherein applying the second electrical signal comprises applying the second electrical signal according to a predetermined duration independent of a change in the indication of the acute event.

8. The method of claim 1, wherein the first electrical signal has a pulse range from about 2 pulses to about 10 pulses and has a microburst duration less than about 100 msec.

9. The method of claim 1, wherein the first electrical signal has a pulse range from about 2 pulses to about 6 pulses and has a microburst duration from about 20 msec to about 80 msec.

10. The method of claim 1, wherein applying the first electrical signal to the cranial nerve comprises applying the first electrical signal to at least one of a left vagus nerve or a right vagus nerve.

11. An implantable medical device comprising a memory coupled to a processor, the memory having instructions stored thereon that, when executed by the processor, cause the implantable medical device to:
    apply a first electrical signal including at least one microburst of a plurality of pulses during a first time period to treat a medical condition of a patient, the first period being a time period during which there is no indication that an acute condition has occurred;
    detect an indication of an acute event associated with the medical condition based on at least one factor preprogrammed to the implantable medical device, the at least one preprogrammed factor comprising at least one physiological characteristic particular to the patient; and
    apply a second electrical signal to treat the medical condition in response to the indication of the acute event and for treating the acute event, the second electrical signal including at least one burst of a second plurality of pulses during a second time period that is a non-microburst, wherein the first time period occurs prior to the second time period.

12. The implantable medical device of claim 11, wherein the instructions further cause the processor to:
    monitor the at least one physiological characteristic during application of the second electrical signal to determine whether the at least one characteristic is active; and
    in response to determining that the at least one physiological characteristic is not active, reapply the first electrical signal.

13. The implantable medical device of claim 11, wherein the at least one physiological characteristic particular to the patient comprises a heart rate deviancy that precedes a seizure for the patient.

14. The implantable medical device of claim 11, wherein the indication is an indication that an epileptic seizure has occurred, an indication that the epileptic seizure is substantially imminent, or an indication that an imminent occurrence of the epileptic seizure is highly probable; and
    wherein the instructions cause the processor to apply the first electrical signal to provide a chronic treatment for an epilepsy condition.

15. The implantable medical device of claim 11, wherein the instructions cause the processor to detect the indication of the acute event by:
    sensing at least one body parameter associated with the at least one physical characteristic; and applying a seizure detection algorithm to the at least one sensed body parameter to detect the indication of the acute event;

wherein the at least one body parameter comprises at least one of a heart rate parameter, a temperature, an EEG signal, a breathing rate, or an eye parameter.

16. An implantable medical device for treating a medical condition in a patient, the implantable medical device comprising:

an implantable electrical signal generator configured to generate electrical signals;

at least one lead coupled to the electrical signal generator and configured to apply the electrical signals to a cranial nerve of the patient;

a processor; and a memory coupled to the processor and having instructions stored thereon that, when executed by the processor, cause the implantable medical device to:

apply, by the at least one lead, a first electrical signal including at least one microburst of a plurality of pulses during a first time period to treat a medical condition of a patient, the first period being a time period during which there is no indication that an acute condition has occurred;

detect an indication of an acute event associated with the medical condition based on at least one factor preprogrammed to the implantable medical device, the at least one preprogrammed factor comprising at least one physiological characteristic particular to the patient;

apply, by the at least one lead, a second electrical signal to treat the medical condition in response to the indication of the acute event and for treating the acute event, the second electrical signal including at least one burst of a second plurality of pulses during a second time period that is a non-microburst, wherein the first time period occurs prior to the second time period;

monitor the at least one physiological characteristic during application of the second electrical signal to determine whether the at least one characteristic is active; and in response to determining that the at least one physiological characteristic is not active, reapply the first electrical signal.

17. The implantable medical device of claim 16, wherein the at least one physiological characteristic particular to the patient comprises a heart rate deviancy that precedes a seizure for the patient.

18. The implantable medical device of claim 16, wherein the at least one lead is configured to apply electrical signals to at least one of a left vagus nerve or a right vagus nerve of the patient; and wherein the instructions cause the processor to apply the first electrical signal to at least one of the left vagus nerve or the right vagus nerve.

19. The implantable medical device of claim 16, wherein the at least one lead is configured to apply electrical signals to at least one of a left vagus nerve or a right vagus nerve of the patient; and wherein the instructions cause the processor to apply the second electrical signal to at least one of the left vagus nerve or the right vagus nerve.

* * * * *